(12) United States Patent
Morris et al.

(10) Patent No.: US 9,833,431 B2
(45) Date of Patent: Dec. 5, 2017

(54) PHARMACEUTICAL COMBINATIONS FOR THE TREATMENT OF CANCER

(71) Applicant: Pitney Pharmaceuticals Pty Limited, Claremont, WA (AU)

(72) Inventors: David Lawson Morris, Lugarno (AU); Mohammad Hossein Pourgholami, Penshurst (AU); Roger Aston, Docklands (AU)

(73) Assignee: Pitney Pharmaceuticals Pty Limited (AU)

( * ) Notice: Subject to any disclaimer, the term of this patent is extended or adjusted under 35 U.S.C. 154(b) by 0 days.

(21) Appl. No.: 15/021,217

(22) PCT Filed: Oct. 31, 2014

(86) PCT No.: PCT/AU2014/001017
§ 371 (c)(1),
(2) Date: Mar. 10, 2016

(87) PCT Pub. No.: WO2015/061832
PCT Pub. Date: May 7, 2015

(65) Prior Publication Data
US 2016/0228399 A1    Aug. 11, 2016

(30) Foreign Application Priority Data
Nov. 1, 2013 (AU) ................ 2013904239

(51) Int. Cl.

| | |
|---|---|
| A01N 47/10 | (2006.01) |
| A61K 31/34 | (2006.01) |
| A61K 31/277 | (2006.01) |
| A61K 31/337 | (2006.01) |
| A61K 31/513 | (2006.01) |
| A61K 31/65 | (2006.01) |
| A61K 31/704 | (2006.01) |
| A61K 31/7068 | (2006.01) |
| A61K 31/138 | (2006.01) |
| A61K 31/167 | (2006.01) |
| A61K 31/17 | (2006.01) |
| A61K 31/40 | (2006.01) |
| A61K 31/4045 | (2006.01) |
| A61K 31/4184 | (2006.01) |
| A61K 31/429 | (2006.01) |
| A61K 31/4965 | (2006.01) |
| A61K 31/5415 | (2006.01) |
| A61K 31/5513 | (2006.01) |
| A61K 31/567 | (2006.01) |
| A61K 31/585 | (2006.01) |
| A61K 31/275 | (2006.01) |
| C07C 255/29 | (2006.01) |
| C07C 323/62 | (2006.01) |
| C07C 317/44 | (2006.01) |

(52) U.S. Cl.
CPC .......... *A61K 31/277* (2013.01); *A61K 31/138* (2013.01); *A61K 31/167* (2013.01); *A61K 31/17* (2013.01); *A61K 31/337* (2013.01); *A61K 31/40* (2013.01); *A61K 31/4045* (2013.01); *A61K 31/4184* (2013.01); *A61K 31/429* (2013.01); *A61K 31/4965* (2013.01); *A61K 31/513* (2013.01); *A61K 31/5415* (2013.01); *A61K 31/5513* (2013.01); *A61K 31/567* (2013.01); *A61K 31/585* (2013.01); *A61K 31/65* (2013.01); *A61K 31/704* (2013.01); *A61K 31/7068* (2013.01); *A61K 31/275* (2013.01); *C07C 255/29* (2013.01); *C07C 317/44* (2013.01); *C07C 323/62* (2013.01)

(58) Field of Classification Search
None
See application file for complete search history.

(56) References Cited

FOREIGN PATENT DOCUMENTS

WO    2013/138863    9/2013

OTHER PUBLICATIONS

Shah et al. Seminars in Oncology (2004), vol. 31, pp. 574-587.*
International Search Report and Written Opinion mailed on dated Dec. 8, 2014 for PCT Application No. PCT/AU2014/001017, 7 pages.

* cited by examiner

*Primary Examiner* — Patrick Lewis
(74) *Attorney, Agent, or Firm* — Kilpatrick Townsend & Stockton LLP

(57) ABSTRACT

The present invention relates to pharmaceutical combinations comprising aminoacetonitrile derivatives and anticancer compounds. Further, the present invention relates to these pharmaceutical combinations for use in the treatment of cancer.

14 Claims, 28 Drawing Sheets

PHARMACEUTICAL COMBINATIONS FOR THE TREATMENT OF CANCER

Cross-Reference to Related Applications

This application is a national stage entry under 35 U.S.C. §371 of International Application No. PCT/AU2014/001017, filed Oct. 31, 2014, which claims priority to Australian Patent Application No. 2013904239, filed Nov. 1, 2013.

FIELD

The present invention relates to pharmaceutical combinations comprising aminoacetonitrile derivatives and anticancer compounds. Further, the present invention relates to these pharmaceutical combinations for use in the treatment of cancer.

BACKGROUND

Aminoacetonitrile derivatives (AADS) are a class of anthelmintics effective against drug-resistant nematodes. The nematodes, or roundworms, comprise a large number of w pathogens of man and domestic animals. Gastrointestinal nematodes, such as *Haemanchus contortus*, are major parasites of ruminants that cause substantial economic losses to livestock production worldwide.

Monepantel (MPL) (N-[(1S)-1-cyano-2-(5-cyano-2-trifluoromethyl-phenoxy)-1-methyl-ethyl]-4-trifluoromethyl-sulfanyl-benzamide) is an example of such an AAD and has been approved as a nematocide for the treatment of sheep gastrointestinal parasites.

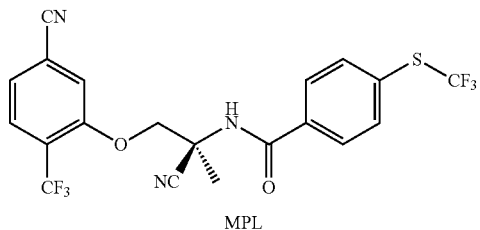 [SMILES: C[C@](C#N)(COc1cc(C#N)ccc1C(F)(F)F)NC(=O)c1ccc(SC(F)(F)F)cc1]

MPL

MPL has been shown to be efficacious against various species of livestock-pathogenic nematodes.

It has now surprisingly been found that the combination of aminoacetonitrile derivatives (AADs), and other anticancer compounds dramatically enhances the efficacy of the anticancer compounds in the treatment of cancer.

SUMMARY OF INVENTION

According to a first aspect of the present invention there is provided a pharmaceutical composition comprising a synergistic combination of at least one aminoacetonitrile derivative, or a metabolite, pharmaceutically acceptable salt, solvate or prodrug thereof, and at least one anticancer compound, or a metabolite, pharmaceutically acceptable salt, solvate or prodrug thereof.

According to a second aspect of the present invention there is provided a pharmaceutical composition according to the first aspect of the invention for the treatment of cancer.

According to a third aspect of the present invention there is provided a method for the treatment of cancer, the method comprising administering a therapeutically effective amount of the pharmaceutical composition according to according to the first aspect of the invention to a patient in need thereof.

According to a fourth aspect of the present invention there is provided use of the pharmaceutical composition according to according to the first aspect of the invention for the manufacture of a medicament for the treatment of cancer.

According to a fifth aspect of the present invention there is provided use of at least one aminoacetonitrile derivative, or a metabolite, pharmaceutically acceptable salt, solvate or prodrug thereof, for enhancing the therapeutic efficacy of an anticancer compound in an anticancer regimen.

According to a sixth aspect of the present invention there is provided use of at least one aminoacetonitrile derivative, or a metabolite, pharmaceutically acceptable salt, solvate or prodrug thereof, for reducing the dose of an anticancer compound in an anticancer regimen.

According to a seventh aspect of the present invention there is provided use of at least one aminoacetonitrile derivative, or a metabolite, pharmaceutically acceptable salt, solvate or prodrug thereof, for reducing the side effects of an anticancer compound in an anticancer regimen.

According to an eighth aspect of the present invention there is provided a method for enhancing the therapeutic efficacy of an anticancer compound in an anticancer regimen, comprising administering a therapeutically effective amount of at least one aminoacetonitrile derivative, or a metabolite, pharmaceutically acceptable salt, solvate or prodrug thereof.

According to a ninth aspect of the present invention there is provided a method for reducing the dose of an anticancer compound in an anticancer regimen, comprising administering a therapeutically effective amount of at least one aminoacetonitrile derivative, or a metabolite, pharmaceutically acceptable salt, solvate or prodrug thereof.

According to a tenth aspect of the present invention there is provided a method for reducing the side effects of an anticancer compound in an anticancer regimen, comprising administering a therapeutically effective amount of at least one aminoacetonitrile derivative, or a metabolite, pharmaceutically acceptable salt, solvate or prodrug thereof.

According to an eleventh aspect of the present invention there is provided use of at least one aminoacetonitrile derivative, or a metabolite, pharmaceutically acceptable salt, solvate or prodrug thereof, in the manufacture of a medicament for enhancing the therapeutic efficacy of an anticancer compound in an anticancer regimen.

According to a twelfth aspect of the present invention there is provided use of at least one aminoacetonitrile derivative, or a metabolite, pharmaceutically acceptable salt, solvate or prodrug thereof, in the manufacture of a medicament for reducing the dose of an anticancer compound in an anticancer regimen.

According to a thirteenth aspect of the present invention there is provided use of at least one aminoacetonitrile derivative, or a metabolite, pharmaceutically acceptable salt, solvate or prodrug thereof, in the manufacture of a medicament for reducing the side effects of an anticancer compound in an anticancer regimen.

DESCRIPTION OF EMBODIMENTS

Figure 1:
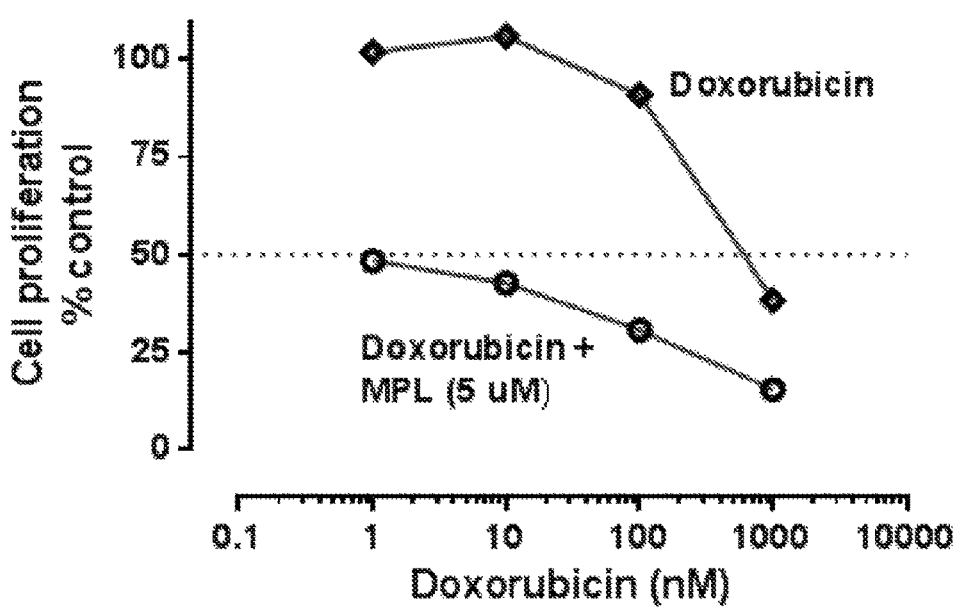
FIG. 1 shows the combined effect of doxorubicin and MPL on cell proliferation in A2780 cells. The addition of 5 μM MPL to doxycycline treatment schedule reduced the IC50 value from 500 to 1 nM (approximate values). Doxorubicin (10 nM) in the presence of MPL (5 μM) is equivalent to doxorubicin at 1000 nM in the absence of MPL.

The aminoacetonitrile derivatives (AADs) that may be employed according to the present invention have the following structure:

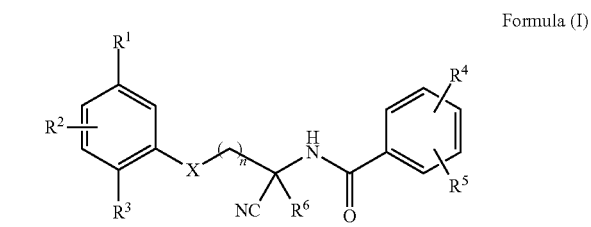

Formula (I)

Preferably, $R^1$ is —CN, H or halogen. More preferably, $R^1$ is —CN. Preferably, $R^2$ is H or halogen, and more preferably H. Preferably, $R^3$ is —$CF_3$ or halogen and more preferably —$CF_3$. Preferably, $R^4$ is —$SCF_3$, —$SOCF_3$, —$SO_2CF_3$, —$OCF_3$ or —$CF_3$. More preferably, $R^4$ is —$SCF_3$ or —$SO_2CF_3$. Preferably, $R^5$ is H. Preferably, $R^6$ is alkyl and more preferably $CH_3$. Preferably, X is O. Preferably, n is 1 to 15, 1 to 10, 1 to 5, 1 to 2, or 1. Most preferably, n is 1. Preferably, $R^4$ is arranged para to the amide moiety.

The compound of formula (I) may be the (R)— or (S)-enantiomer or the racemate.

The compound of formula (I) may be selected from any one of the following compounds:

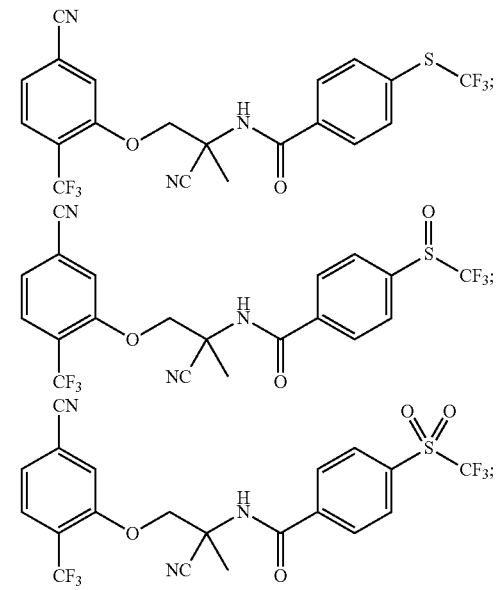

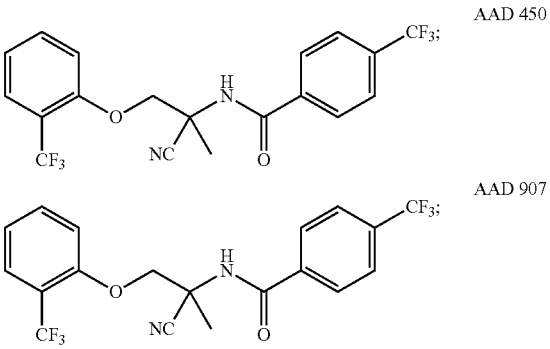

AAD 450

AAD 907

-continued

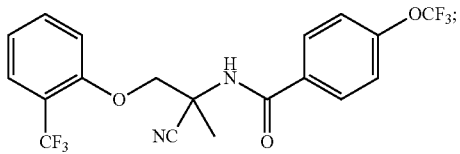
AAD 970

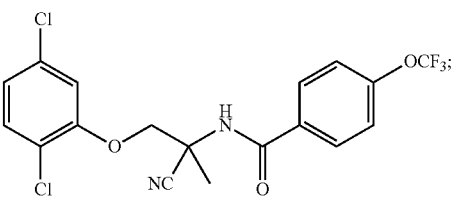
AAD 1154

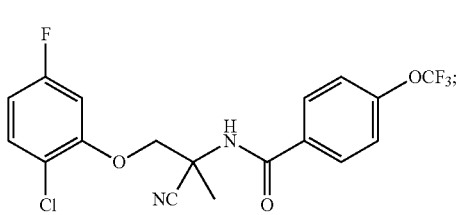
AAD 004

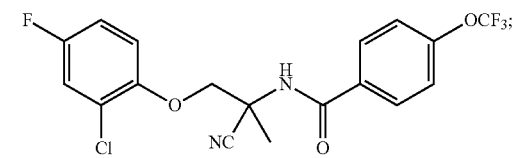
AAD 2009

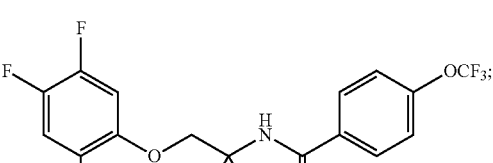
AAD 1336

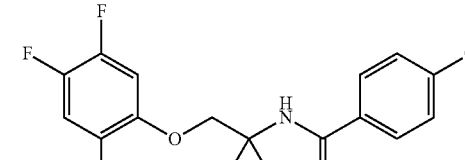
AAD 1470 wherein each of the above compounds is the (R)— or (S)-enantiomer, or the racemate, or a metabolite, pharmaceutically acceptable salt, solvate or prodrug thereof.

Preferably, the compound of formula (I) may be selected from any one of the following compounds:

AAD 2224

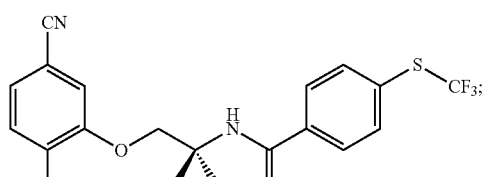
(MPL-(R))

-continued

AAD 907

AAD 1336

AAD 1470 wherein each of the above compounds is the (R)— or (S)-enantiomer, or the racemate, (unless specified) or a metabolite, pharmaceutically acceptable salt, solvate or prodrug thereof.

More preferably, the compound of formula (I) is MPL (N-[(1S)-1-cyano-2-(5-cyano-2-trifluoromethyl-phenoxy)-1-methyl-ethyl]-4-trifluoromethylsulfanyl-benzamide):

MPL or a metabolite, pharmaceutically acceptable salt, solvate or prodrug thereof.

Further, the compound of formula (I) may be a metabolite of MPL, which is monepantel sulphone (MPL-SO₂):

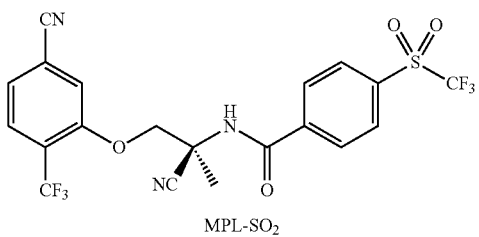 [SMILES: C[C@](C#N)(COc1cc(C#N)ccc1C(F)(F)F)NC(=O)c1ccc(S(=O)(=O)C(F)(F)F)cc1]
MPL-SO₂ or a metabolite, pharmaceutically acceptable salt, solvate or prodrug thereof.

The above exemplary AAD compounds of formula (I) according to the present invention may be summarised according to Table 1 and formula (Ia):

Formula (Ia)

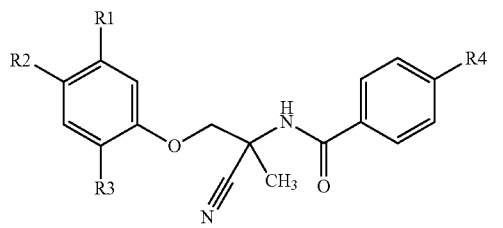

TABLE 1

Amino-acetonitrile derivatives (AADs) according to formula (Ia)

| AAD | R1 | R2 | R3 | R4 |
|---|---|---|---|---|
| 1566 (MPL) | CN | H | $CF_3$ | $SCF_3$ |
| 2105 (MPL-SO) | CN | H | $CF_3$ | $SOCF_3$ |
| 4670 (MPL-$SO_2$) | CN | H | $CF_3$ | $SO_2CF_3$ |
| 450 | H | H | Cl | $CF_3$ |
| 907 | H | H | $CF_3$ | $CF_3$ |
| 970 | H | H | $CF_3$ | $OCF_3$ |
| 1154 | Cl | H | Cl | $OCF_3$ |
| 004 | F | H | Cl | $OCF_3$ |
| 2009 | H | F | Cl | $OCF_3$ |
| 1336 | F | F | Br | $OCF_3$ |
| 1470 | F | F | $CF_3$ | $OCF_3$ |

"MPL-(R)" refers to N-[(1R)-1-cyano-2-(5-cyano-2-trifluoromethyl-phenoxy)-1-methyl-ethyl]-4-trifluoromethyl-sulfanyl-benzamide, and "MPL-(S)" refers to N-[(1S)-1-cyano-2-(5-cyano-2-trifluoromethyl-phenoxy)-1-methyl-ethyl]-4-trifluoromethylsulfanyl-benzamide.

The pharmaceutical combination of the present invention comprises at least one anticancer compound. For example, the anticancer compound may be any drug that modifies or slows cancer cell proliferation and may be selected from the group including cytostatic agents, cytotoxic agents (such as for example, but not limited to, DNA rte interactive agents (such as cisplatin or doxorubicin)); taxanes (e.g. taxotere, taxol) topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Famesyl protein transferase inhibitors (such as, SARASAR™ (4~[2-[4-[(11R)-3,10-dibromo-8-chloro-6,11-dihydro-5H-benzo[5,6]cyclohepta[1,2-b]pyridin-11-yl-]-1-piperidinyl]-2-oxoehtyl]-1-piperidinecarboxamide, or SCH 66336 from Schering-Plough Corporation, Kenilworth, N.J.), tipifamib (Zamestra® or R115777 from Janssen Pharmaceuticals), L778.123 (a famesyl protein transferase inhibitor from Merck & Company, Whitehouse Station, N.J.), BMS 214662 (a famesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, Cytoxan, gemcitabine and the nitrosoureas.

Preferably, the anticancer compound of the pharmaceutical combination of the present invention is selected from at least one of doxorubicin, cisplatin, 5-fluorouracil, etoposide, imatinib, mitomycin C, vincristine, paclitaxel, tamoxifen, minocycline, albendazole, levamisole, flutamide, tamoxifen, wortmannin, oxaliplatin, bortezimib, amiloride, EGTA, enalapril, Mgi32, captopril, cimetidine, mifepristone, glibendamide, trifluoperazine, serotonin, clozapine, gemcitabine, ivermectin, colchicine, rapamycin and everilimus.

Further, the anticancer compound of the pharmaceutical combination of the present invention may be selected from cyclophosphamide, methothrexate, cytarabine, daunorubicin, bleomycin, vinblastine and vindesine.

More preferably, the anticancer compound of the pharmaceutical combination of the present invention is selected from at least one of doxorubicin, cisplatin, 5-fluorouracil, etoposide, imatinib, mitomycin, vincristine, paditaxel, tamoxifen, albendazole, levamisole, flutamide, gemcitabine, oxaliplatin, tamoxifen, colchicine and minocycline.

In one embodiment, the anticancer compound of the pharmaceutical combination of the present invention is doxorubicin.

According to one embodiment, the present invention provides a pharmaceutical composition comprising a synergistic combination of a compound according to Formula I or a metabolite, pharmaceutically acceptable salt, solvate or prodrug thereof and any one or more of doxorubicin, flutamide, gemcitabine, 5-fluorouracil, oxaliplatin, paclitaxel, tamoxifen, colchicine and minocycline.

According to another embodiment, the present invention provides a pharmaceutical composition comprising a synergistic combination of a compound according to Formula I or a metabolite, pharmaceutically acceptable salt, solvate or prodrug thereof, 5-fluorouracil and gemcitabine.

According to another embodiment, the present invention provides a pharmaceutical composition comprising a synergistic combination of a compound according to Formula I or a metabolite, pharmaceutically acceptable salt, solvate or prodrug thereof, minocycline and doxorubicin.

According to another embodiment, the present invention provides a pharmaceutical composition comprising a synergistic combination of a compound according to Formula I or a metabolite, pharmaceutically acceptable salt, solvate or prodrug thereof, minocycline and pacitaxel.

Preferably, the cancer is selected from the following: carcinoma, including that of the bladder, breast, colon, mesothelioma, kidney, liver, lung, including small cell lung cancer, non-small cell lung cancer, head and neck, oesophagus, gall bladder, ovary, pancreas, stomach, cervix, thyroid, prostate, and skin, including squamous cell carcinoma; hematopoietic tumors of lymphoid lineage, including leukaemia, acute lymphocytic leukaemia, acute lymphoblastic leukaemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocyte leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Preferably, the cancer to be treated is selected from cancer of the ovaries, breast, prostate or mesothelioma cancer, and most preferably the cancer to be treated is cancer of the ovaries.

Doxorubicin (trade name Doxil; also known as hydroxydaunorubicin) is a drug used in cancer chemotherapy. It is an anthracycline antibiotic, closely related to the natural product daunomycin. It is commonly used in the treatment of a wide range of cancers, including hematological malignancies, many types of carcinoma, and soft tissue sarcomas.

Cisplatin (cisplatinum, or cis-diamminedichloroplatinum (II)) is a chemotherapy drug. It was the first member of a class of platinum-containing anticancer drugs, which now also includes carboplatin and oxaliplatin. These platinum complexes react in vivo, binding to and causing crosslinking of DNA, which ultimately triggers apoptosis (programmed cell death).

Fluorouracil (or 5-FU) is a chemotherapy agent, which acts principally as a thymidylate synthase inhibitor. Interrupting the action of this enzyme blocks synthesis of the pyrimidine thymidine, which is a nucleoside required for DNA replication. Thymidylate synthase methylates deoxyuridine monophosphate (dUMP) into thymidine monophosphate (dTMP). Administration of 5-FU causes a scarcity in dTMP, so rapidly dividing cancerous cells undergo cell death via thymineless death.

Etoposide forms a ternary complex with DNA and the topoisomerase II enzyme (which aids in DNA unwinding), prevents re-ligation of the DNA strands, and by doing so causes DNA strands to break. Cancer cells rely on this enzyme more than healthy cells, since they divide more rapidly. Therefore, this causes errors in DNA synthesis and promotes apoptosis of the cancer cell.

Imatinib (marketed by Novartis as Gleevec (U.S.) or Glivec (Europe/Australia/Latin America), and sometimes referred to by its investigational name STI-571, is a tyrosine-kinase inhibitor used in the treatment of multiple cancers, most notably Philadelphia chromosome-positive (Ph+) chronic myelogenous leukemia (CML). Like all tyrosine-kinase inhibitors, imatinib works by preventing a tyrosine kinase enzyme, in this case BCR-Abl, from phosphorylating subsequent proteins and initiating the signaling cascade necessary for cancer development, thus preventing the growth of cancer cells and leading to their death by apoptosis. As the BCR-Abl tyrosine kinase enzyme exists only in cancer cells and not in healthy cells, imatinib works as a form of targeted therapy; only cancer cells are killed through the drug's action. In this regard, imatinib was one of the first cancer therapies to show the potential for such targeted action, and is often cited as a paradigm for research in cancer therapeutics.

In humans, caffeine acts as a central nervous system stimulant, temporarily warding off drowsiness and restoring alertness. Caffeine is classified by the Food and Drug Administration as GRAS (generally recognized as safe), as toxic doses (over 1 gram for an average adult) are much higher than typically used doses (less than 500 milligrams). Ordinary consumption can have low health risks, even when carried on for years; there may be a modest protective effect against some diseases, including Parkinsons Disease, and certain types of cancer. Caffeine can have both positive and negative effects on anxiety disorders.

Mitomycin (or mitomycin C) is a chemotherapeutic agent in glaucoma surgery. It is also a potent DNA crosslinker. A single crosslink per genome has shown to be effective in killing bacteria. This is accomplished by reductive activation followed by two N-alkylations. Both alkylations are sequence specific for a guanine nucleoside in the sequence 5'-CpG-3'.

Tubulin is a structural protein that polymerizes to microtubules. The cell cytoskeleton and mitotic spindle, among other things, are made of microtubules. Vincristine binds to tubulin dimers, inhibiting assembly of microtubule structures. Disruption of the microtubules arrests mitosis in metaphase. Therefore, the *vinca* alkaloids affect all rapidly dividing cell types including cancer cells, but also those of intestinal epithelium and bone marrow.

Paclitaxel is a mitotic inhibitor used in cancer chemotherapy.

Tamoxifen is an antagonist of the estrogen receptor in breast tissue via its active metabolite, hydroxytamoxifen. In other tissues such as the endometrium, it behaves as an agonist, and thus may be characterized as a mixed agonist/antagonist. Tamoxifen is the usual endocrine (anti-estrogen) therapy for hormone receptor-positive breast cancer in pre-menopausal women, and is also a standard in post-menopausal women.

Cimetidine, approved by the FDA for inhibition of gastric acid secretion, has been advocated for a number of dermatological diseases. Cimetidine was the prototypical histamine H2-receptor antagonist from which the later members of the class were developed.

Mifepristone is a synthetic steroid compound used as a pharmaceutical. It is a progesterone receptor antagonist used as an abortifacient in the first months of pregnancy, and in smaller doses as an emergency contraceptive. Mifepristone is also a powerful glucocorticoid receptor antagonist, and has occasionally been used in refractory Cushing's Syndrome (due to ectopic/neoplastic ACTH/Cortisol secretion). During early trials, it was known as RU-38486 or simply RU-486. It is marketed under trade names Korlym and Mifeprex.

In the present invention, the cytotoxicity of certain anticancer compounds is enhanced by the addition of aminoacetonitrile derivatives, such as MPL. This is important because:

if the dose of an anticancer drug may be reduced, it may be safer and more beneficial to the patient, and result in a reduction in side effects of chemotherapy (for example, the enhancement of doxorubicin activity without the associated cardiac toxicity);

MPL has no toxicity so the enhancement is very different to that which may be seen by mixing two anticancer drugs;

it may be possible to administer MPL or drug selectively to tumours through organ vasculature so as to maximise enhancement of cytotoxicity in a localised manner (particularly relevant in brain or liver tissue); and the use of MPL may be particularly relevant in situations where drug resistance has developed and one normally cannot increase dose of the chemotherapy.

One of the greatest challenges in medicine during that past 50 years has been the identification of drugs that can effectively kill tumour cells without harming normal tissues. The side-effect profile of almost all known classes of anticancer drug is substantive in limiting the physician's ability to treat the cancer patient, especially at late stages when resistance to the drug often develops. In such cases of drug resistance, the option of increasing the dose of cytotoxic chemotherapy is limited by the toxicity in normal tissues. By enhancing the specific activity of known chemotherapeutic agents by up to 100-fold through the use of AADs as described in the present invention, this provides the physician with the option of increasing chemotherapy without associated side effects. In other words, the pharmaceutical composition of the present invention enhances the activity of the anticancer compound by up to 100-fold, without enhancing the toxicity of the anticancer compound to the same degree.

Accordingly, the present invention reduces the adverse events associated with chemotherapy by selectively enhancing the anticancer activity of chemotherapeutic agents, and not affecting the cytotoxic activity on normal tissues. Such adverse effects include:

Immunosuppression and myelosuppression
Typhlitis
Gastrointestinal distress
Anemia
Fatigue
Chemotherapy-induced nausea and vomiting
Hair loss
Secondary neoplasm
Infertility
Teratogenicity
Neurological adverse effects
Tumor lysis syndrome
Organ damage
Cachexia
Weight loss
Cardiotoxicity The enhanced cytotoxicity afforded by AADs is not limited to anticancer drugs conventionally used in chemotherapy. It has been shown here that other drugs that interfere with metabolism also benefit from significant enhancement.

The degree of enhancement observed depends on the nature and mechanism of action of the anticancer compound. The use of combinations of AADs and anticancer compounds may be achieved either by administering a mixture of the two drugs or through individual sequential administration.

Although AADs can dramatically enhance the cytotoxic activities of chemotherapeutic drugs in cancer cells, this enhancement of cytotoxicity is not seen with normal cells. As such, the present invention lends itself to the treatments of cancer, drug resistant cancers and in reducing the side effects of chemotherapy. Thus, by maintaining the cytotoxicity of a chemotherapeutic agent against cancer at a much smaller dose than normally prescribed without enhancing toxicity to normal cells enables the elimination of drug-mediated side effects in cancer therapy.

According to the present invention, a treatment regimen may be developed whereby the optimal therapeutic index can be achieved in the treatment of cancer with chemotherapy or drugs which interfere with cancer cell metabolism. Further, a treatment regimen that optimizes the chronology of treatment with AADs and a cancer treating drug may be developed.

Definitions

"Halogen" means fluorine, chlorine, bromine or iodine, preferably fluorine or chlorine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Aryl" by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl. The term "aryl" also includes fused cyclic hydrocarbon rings which are partially aromatic (i.e., one of the fused rings is aromatic and the other is non-aromatic). An exemplary aryl group which is partially aromatic is indanyl.

"Heteroaryl," by itself or as part of another substituent, means a cyclic or polycyclic group having from five to twelve ring atoms selected from C, N, O and S. wherein at least one ring heteroatom is O, N or S, and wherein at least one of the constituent rings is aromatic. Exemplary heteroaryl groups for use in the invention include carbazolyl, carbolinlyl, chromenyl, cinnolinyl, furanyl, benzofuranyl, benzofurazanyl, isobenzofuranyl, imidazolyl, benzimidazolyl, benzimidazolonyl, indazolyl, indolyl, isoindolyl, indolinyl, indolazinyl, indynyl, oxadiazolyl, oxazolyl, benzoxazolyl, isoxazolyl, pyranyl, pyrazinyl, pyrazolyl, benzopyrazolyl, pyridazinyl, pyridyl, pyrimidinyl, pyrrolyl, quinolyl, isoquinolyl, tetrazolyl, thiazolyl, isothiazolyl, thiadiazolyl, thienyl, benzothioenyl, benzothiazolyl, quinoxalinyl, triazinyl and triazolyl, and N-oxides thereof.

One subgroup of heteroaryl groups have 5 ring atoms. Exemplary heteroaryl groups in this embodiment are pyrazolyl, pyridyl, thiazolyl and imidazolyl.

Another subgroup of heteroaryl groups have 6 ring atoms. Exemplary heteroaryl groups in this embodiment are pyridinyl and pyrimidinyl.

The term "heteroaryl" also includes fused cyclic heterocyclic rings which are partially aromatic (i.e., one of the fused rings is aromatic and the other is non-aromatic). An exemplary heteroaryl group which is partially aromatic is benzodioxol.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

"Heteroatom" means an atom selected from N, O, P and S. Where necessary, any undesignated valency is independently selected from H, OH, carbonyl, n-alkyl or alkoxy.

"n" may be 1 to 20, preferably 1 to 10, more preferably 1 to 6, and most preferably 1 to 4.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flow ability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options, meaning that more than one substituent may be present simultaneously at various sites.

"Prodrugs" and "solvates" of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of the present invention or a metabolite, pharmaceutically acceptable salt or solvate of the compound. The transformation may occur by various mechanisms (e.g., by metabolic or chemical processes). A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

"Metabolites" of the compounds of the invention refer to the intermediates and products of metabolism.

The compounds of formula (I) may contain asymmetric or chiral centres, and, therefore, exist in different stereoisomeric forms. It is intended that all stereoisomeric forms of the compounds of formula (I) as well as mixtures thereof, including mixtures, form part of the present invention. In addition, the present invention embraces all geometric and positional isomers. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolysing) the individual diastereomers to the corresponding pure enantiomers. Enantiomers can also be separated by use of chiral HPLC column. The chiral centres of the present invention can have the S or R configuration as defined by the IUPAC 1974.

The use of the terms "salt", "solvate", or "prodrug" and the like, is intended to equally apply to the salt, solvate and prodrug of enantiomers, stereoisomers, rotamers, tautomers, positional isomers, racemates or prodrugs of the inventive compounds.

The terms "synergy", "synergistic", "synergistic effect" and "synergistic combination" as used herein refers to a mixture of two or more discrete agents which, when combined, display a degree of anticancer activity, such as anti-proliferative activity or cytotoxicity etc., which is greater than the expected additive effect of said agents. The terms also refer to the combined effect of administering an amount of one therapeutic agent that, when administered alone, produces no significant response but, when administered in combination with another therapeutic compound, produces an overall response that is significantly greater than that produced by the second compound alone.

The term "anticancer", as used herein, is intended to refer to the activity of suppressing the formation or growth of cancer cells, killing cancer cells, or inhibiting or blocking the metastasis of cancer cells, encompassing the meaning of the inhibition of cancer cell metastasis as well as the prophylaxis and treatment of cancer.

As used in this application, the singular form "a", "an" and "the" include plural references unless the context dearly dictates otherwise.

As used herein, the term "comprising" means "including." Variations of the word "comprising", such as "comprise" and "comprises," have correspondingly varied meanings. Thus, for example, a pharmaceutical composition "comprising" a compound of formula (I) may consist exclusively of that compound or may include one or more additional components (e.g. a pharmaceutically acceptable carrier, excipient and/or diluent).

As used herein the term "plurality" means more than one. In certain specific aspects or embodiments, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

"Therapeutically effective amount" means an amount of at least one compound of the present invention, or a metabolite, pharmaceutically acceptable salt, solvate or prodrug thereof, that substantially inhibits proliferation and/or prevents differentiation of a human tumor cell, including human tumor cell lines. The term "therapeutically effective amount" as used herein, includes within its meaning a non-toxic but sufficient amount of an agent or composition for use in the present invention to provide the desired therapeutic effect. The exact amount required will vary from subject to subject depending on factors such as the species being treated, the age and general condition of the subject, the severity of the condition being treated, the particular agent being administered, the mode of administration and so forth. Thus, it is not possible to specify an exact "effective amount" applicable to all embodiments. However, for any given case, an appropriate "effective amount" may be determined by one of ordinary skill in the art using only routine experimentation.

Detailed Description

The AADs (e.g. formula (I)) are a class of compounds that may be synthesized using the ordinary knowledge of organic synthetic methodology. For example, the AADs may be synthesised by derivitisation of phenols with chloroacetone, Strecker reaction and acylation of the resultant amine with aroyl chlorides (as shown in Scheme 1). Where necessary, a particular enantiomer may then be obtained, for example, by chiral resolution (as shown in Scheme 2).

Scheme 1:

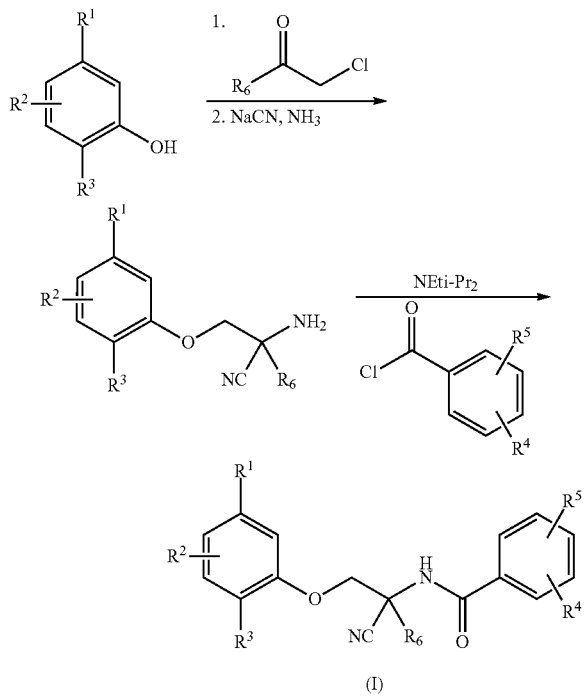

Scheme 2:

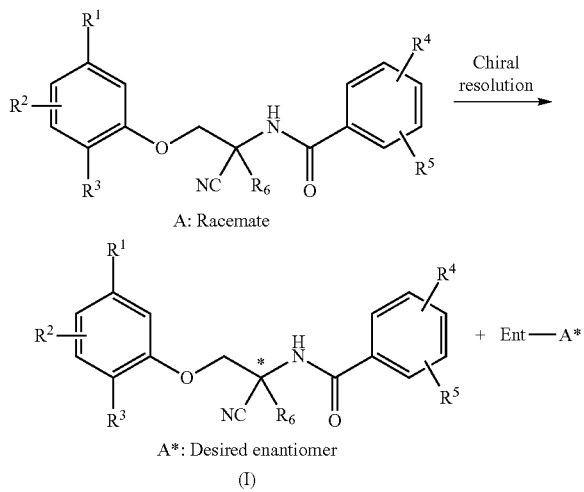

Compositions, Medicaments and Kits

The present invention provides pharmaceutical compositions, medicaments and kits which comprise at least one aminoacetonitrile derivative, or a metabolite, pharmaceutically acceptable salt, solvate or prodrug of said compound, at least one further anticancer compound, or a metabolite, pharmaceutically acceptable salt, solvate or prodrug of said compound, and at least one pharmaceutically acceptable carrier. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Compositions and medicaments of the present invention may be in a form suitable for administration by injection (e.g. for parenteral administration including subcutaneous, intramuscular, intraperitoneal or intravenous injection), by oral administration (such as capsules, tablets, caplets, and elixirs, for example), by topical administration (e.g. in the form of an ointment, cream or lotion, or a form suitable for delivery as an eye drop), or by intranasal inhalation (e.g. in the form of aerosols).

Liquid form preparations include solutions, suspensions and emulsions, for example water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen. Also included are solid form preparations that are intended to be converted, shortly before use, to liquid form preparations for either oral or parenteral administration. Such liquid forms include solutions, suspensions and emulsions.

The pharmaceutical combinations of the invention may also be deliverable transdermally. The transdermal compositions can take the form of creams, lotions, aerosols and/or emulsions and can be included in a transdermal patch of the matrix or reservoir type as are conventional in the art for this purpose.

The pharmaceutical combinations of this invention may also be delivered subcutaneously.

In one embodiment, the pharmaceutical combinations of the present invention are administered into the body intraperitoneally.

Compositions and medicaments of the present invention may comprise a pharmaceutically acceptable carrier, adjuvant, excipient and/or diluent. The carriers, diluents, excipients and adjuvants must be "acceptable" in terms of being compatible with the other ingredients of the composition or medicament, and are generally not deleterious to the recipient thereof. Non-limiting examples of pharmaceutically acceptable carriers or diluents are demineralised or distilled water; saline solution; vegetable based oils such as peanut oil, safflower oil, olive oil, cottonseed oil, maize oil; sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxylpropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from about 10% to about 99.9% by weight of the composition or medicament.

For administration as an injectable solution or suspension, non-toxic parenterally acceptable diluents or carriers can include, Ringer's solution, isotonic saline, phosphate buffered saline, ethanol and 1,2 propylene glycol. Methods for preparing parenterally administrable compositions and medicaments are apparent to those of ordinary skill in the art, and are described in more detail in, for example, Remington's Pharmaceutical Science, 15th ed., Mack Publishing Company, Easton, Pa.

For oral administration, some examples of suitable carriers, diluents, excipients and adjuvants include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl stearate which delay disintegration. Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Formulations for oral administration may comprise one or more emulsifying agents. Suitable emulsifying agents include dispersing agents as exemplified above or natural gums such as guar gum, gum acacia or gum tragacanth.

Topical formulations of the present invention may comprise an active ingredient together with one or more acceptable carriers, and optionally any other therapeutic ingredients. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil, wool fat or its derivatives, or a fatty acid such as stearic or oleic acid together with an alcohol such as propylene glycol or macrogols.

Compositions and medicaments of the present invention may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Compositions and medicaments of the present invention may be administered in the form of a liposome. Suitable methods to form liposomes are known in the art, and in relation to this specific reference is made to Prescott, (Ed), (1976), "Methods in Cell Biology", Volume XIV, Academic Press, New York, N.Y. p. 33 at seq.

Supplementary active ingredients such as adjuvants or biological response modifiers can also be incorporated into compositions and medicaments of the present invention.

Any suitable adjuvant may be included in compositions and medicaments of the present invention. For example, an aluminium-based adjuvant may be utilised. Suitable aluminium-based adjuvants include, but are not limited to, aluminium hydroxide, aluminium phosphate and combinations thereof. Other specific examples of aluminium-based adjuvants that may be utilised are described in European Patent No. 1216053 and U.S. Pat. No. 6,372,223. Other suitable adjuvants include Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminium salts such as aluminium hydroxide gel (alum) or aluminium phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; oil in water emulsions including those described in European Patent No. 0399843, U.S. Pat. No. 7,029,678 and PCT Publication No. WO 2007/006939; and/or additional cytokines, such as GM-CSF or interleukin-2, -7, or -12, granulocyte-macrophage colony-stimulating factor (GM-CSF), monophosphoryl lipid A (MPL), cholera toxin (CT) or its constituent subunit, heat labile enterotoxin (LT) or its constituent subunit, toll-like receptor ligand adjuvants such as lipopolysaccharide (LPS) and derivatives thereof (e.g. monophosphoryl lipid A and 3-Deacylated monophosphoryl lipid A), muramyl dipeptide (MDP) and F protein of Respiratory Syncytial Virus (RSV).

Another aspect of this invention is a kit comprising a therapeutically effective amount of at least one aminoacetonitrile derivative, or a metabolite, pharmaceutically acceptable salt, solvate or prodrug of said compound, at least one anticancer compound, or a metabolite, pharmaceutically acceptable salt, solvate or prodrug of said compound, and a pharmaceutically acceptable carrier, vehicle or diluent.

Another aspect of this invention is a kit comprising an amount of at least one aminoacetonitrile derivative, or a metabolite, pharmaceutically acceptable salt, solvate or prodrug of said compound, at least one anticancer compound, or a metabolite, pharmaceutically acceptable salt, solvate or prodrug of said compound, and an amount of at least one anticancer therapy listed above, wherein the amounts of the two or more ingredients result in desired therapeutic effect.

Kits of the present invention may comprise components to assist in performing the methods of the present invention such as, for example, administration device(s), buffer(s), and/or diluent(s). The kits may include containers for housing the various components and instructions for using the kit components in the methods of the present invention.

In certain embodiments, the kits may be combined kits.

In other embodiments, the kits may be fragmented kits.

Dosages and Routes of Administration

The agents, compositions and medicaments can be administered to a recipient by standard routes, including, but not limited to, parenteral (e.g. intravenous, intraspinal, subcutaneous or intramuscular), oral, topical, or mucosal routes (e.g. intranasal). In some embodiments, they may be administered to a recipient in isolation or in combination with other additional therapeutic agent(s). In such embodiments the administration may be simultaneous or sequential.

In general, the agents, compositions and medicaments can be administered in a manner compatible with the route of administration and physical characteristics of the recipient (including health status) and in such a way that the desired effect(s) are induced (i.e. therapeutically effective, immunogenic and/or protective). For example, the appropriate dosage may depend on a variety of factors including, but not limited to, a subject's physical characteristics (e.g. age, weight, sex), whether the agent, composition or medicament is being used as single agent or adjuvant therapy, the progression (i.e. pathological state) of the cancer being treated, and other factors readily apparent to those of ordinary skill in the art.

Various general considerations when determining an appropriate dosage of the agents, compositions and medicaments are described, for example, in Gennaro et al. (Eds), (1990), "Remington's Pharmaceutical Sciences", Mack Publishing Co., Easton, Pa., USA; and Gilman et al., (Eds), (1990), "Goodman And Gilman's: The Pharmacological Bases of Therapeutics", Pergamon Press.

Compounds of formula (I) generally reflect a low toxicity. For example, MPL has single-dose toxicity in excess of 2000 mg per kg of body weight.

Further, there is a generally high clinical tolerance of compounds of formula (I) for the treatment of cancer. For example, a dosage of 1000 mg of MPL per kg of body weight per 24 hours is well tolerated in mammals.

Generally, an effective dosage is expected to be in the range of about 0.0001 mg to about 1000 mg of active component(s) per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; or about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; or about 5.0 mg to about 15 mg per kg body weight per 24 hours.

For example, a preferred dosage may be about 1-100 mg, 50 mg, 2.5-10 mg, or a standard therapeutic dose or range of the compound of formula (I) per kg of body weight per 24 hours. The adopted therapeutic doses of anticancer compounds currently used in cancer therapy can vary widely depending on the cancer and the therapeutic drug. Optimizing the dose of the anticancer compound in the presence of the AAD can be determined by physicians on a case-by-case basis.

Typically, in treatment applications, the treatment may be for the duration of the cancer. Further, it will be apparent to one of ordinary skill in the art that the optimal quantity and spacing of individual dosages can be determined by the nature and extent of the disease state or condition being treated, the form, route and site of administration, and the nature of the particular subject being treated. Optimum dosages can be determined using conventional techniques.

It is intended that anticancer compounds used for treating the types of cancer for which they are normally utilized, e.g. first and second line standard of care drugs. In one embodiment, the anticancer compounds are provided or administered in their normal doses, in which case the provision or administration of an AAD described herein primarily increases the therapeutic efficacy of the agent.

In one embodiment the therapeutic efficacy of an anticancer compound may be enhanced by about 10% to about 2000%. In one embodiment the therapeutic effect may be enhanced by about 10%, 20%, 30%, 40%, 50%, 60%, 70%, 80%, 90%, 100%, 150%, 200%, 250%, 300%, 350%, 400%, 450%, 500%, 550%, 600%, 650%, 700%. 750%, 800%, 850%, 900%, 950%, 1000%, 1050%, 1100%, 1150%, 1200%, 1250%, 1300%, 1350%, 1400%, 1450%, 1500%, 1550%, 1600%, 1650%, 1700%, 1750%, 1800%, 1850%, 1900%, 1950% or about 2000%.

In a preferred embodiment, the therapeutic efficacy of at least one of doxorubicin, cisplatin, 5-fluorouracil, etoposide, imatinib, mitomycin C, vincristine, paditaxel, tamoxifen, minocycline, albendazole, levamisole, flutamide, tamoxifen, wortmannin, oxaliplatin, bortezimib, amiloride, EGTA, enalapril, Mg132, captopril, cimetidine, mifepristone, glibenclamide, trifluoperazine, serotonin, clozapine, gemcitabine, ivermectin, colchicine, rapamycin and everilimus is enhanced.

In another embodiment, the dose of an anticancer compound may be provided or administered at a reduced dose when combined with an AAD. Such dose reduction or enhancement of therapeutic efficacy of the anticancer compound Such enhancement may permit the use of particular anticancer compound for treating a cancer for which the agent is not currently standard therapy. The reduction in the dose of an anticancer compound in a synergistic combination with an AAD may also reduce the side effects of the anticancer compound.

In one embodiment of the dose of an anticancer compound present in a synergistic combination of the invention or used in an anticancer regimen may be reduced by about 2-fold, to about 100-fold. In one embodiment, the reduction in dose is about 2-, 3-, 4-, 5-, 6-, 7-, 8-, 9-, 10-, 20-, 30-, 40-, 50, 60-, 70-, 80-, 90-, or about 100-fold.

In a preferred embodiment, the dose of at least one doxorubicin, cisplatin, 5-fluorouracil, etoposide, imatinib, mitomycin C, vincristine, paclitaxel, tamoxifen, minocycline, albendazole, levamisole, flutamide, tamoxifen, wortmannin, oxaliplatin, bortezimib, amiloride, EGTA, enalapril, Mg132, captopril, cimetidine, mifepristone, glibenclamide, trifluoperazine, serotonin, dozapine, gemcitabine, ivermectin, colchicine, rapamycin and everilimus is reduced.

In many instances (e.g. preventative applications), it may be desirable to have several or multiple administrations of an agent, composition or medicament of the present invention which may, for example, be administered 1, 2, 3, 4, 5, 6, 7, 8, 9, 10, or more times. The administrations may be from about one to about twelve week intervals, and in certain embodiments from about one to about four week intervals. Periodic re-administration is also contemplated.

It will also be apparent to one of ordinary skill in the art that the optimal course of administration can be ascertained using conventional course of treatment determination tests.

Where two or more entities (e.g. agents or medicaments) are administered to a subject "in conjunction", they may be administered in a single composition at the same time, or in separate compositions at the same time, or in separate compositions separated in time.

Certain embodiments of the present invention involve administration of the agents, compositions or medicaments in multiple separate doses. Accordingly, the methods for prophylactic and therapeutic treatment described herein encompass the administration of multiple separated doses to a subject, for example, over a defined period of time. Accordingly, in some embodiments the methods include administering a priming dose, which may be followed by a booster dose. The booster may be for the purpose of re-vaccination. In various embodiments, the agent, composition or medicament is administered at least once, twice, three times or more.

The agents, compositions and medicaments may generally be administered in an effective amount to achieve an intended purpose. More specifically, they may be administered in a therapeutically effective amount which means an amount effective to prevent development of, or to alleviate the existing symptoms of, a target disease or condition. Determination of effective amounts is well within the capability of persons of ordinary skill in the art. For example, a therapeutically effective dose of the agents, compositions and medicaments can be estimated initially from cell culture assays. For example, a dose can be formulated in animal models to achieve a circulating concentration range that includes the IC50 as determined in cell culture. Such information can be used to more accurately determine useful doses in humans and other mammalian subjects.

A therapeutically effective dose refers to that amount of the agent, composition or medicament to prevent development of symptoms, ameliorate symptoms and/or prolong the survival of the subject under treatment. Toxicity and therapeutic efficacy of the agents, compositions and medicaments can be determined by standard pharmaceutical assays in cell cultures, and/or experimental animals (e.g. by determination of the LD50 (the dose lethal to 50% of the population) and the ED50 (the dose therapeutically effective in 50% of the population)). The dose ratio between toxic and therapeutic effects is the therapeutic index which can be expressed as the ratio between LD50 and ED50. Agents, compositions and medicaments which exhibit high therapeutic indices are preferred. The data obtained from such cell culture assays and/or animal studies may be used to formulate a range of dosage for use in humans or other mammals. The dosage of such compounds lies preferably within a range of circulating concentrations that include the ED50 with little or no toxicity. The dosage may vary within this range depending upon the dosage form employed and the administration route utilised. The exact formulation, route of administration and dosage can be selected without difficulty by an individual physician in view of the subject's condition (see, for example, Fingl et al., (1975), in "The Pharmacological Basis of Therapeutics", Ch. 1 p. 1). Dosage amount and interval may be adjusted individually to provide plasma levels of the active agent sufficient to achieve and maintain the desired therapeutic effect/s and/or a minimal effective concentration (MEC). Dosages necessary to achieve the MEC will depend on the route of administration and other individual characteristics. Bioassays and/or HPLC assays may be used to determine plasma concentrations.

Dosage intervals may also be determined using MEC value. In general, the agents, compositions and medicaments may be administered using a regimen which maintains plasma levels above the MEC for between about 10%-90% of the time, preferably between 30%-90% and more preferably between about 50%-90%. In embodiments where local administration or selective uptake is utilized, the effective local concentration of the drug may not be related to plasma concentration.

The combination of the invention may also be useful in combination with one or more of anticancer treatments such as radiation therapy (administered together or sequentially).

Subjects

Prophylactic and therapeutic methods of the present invention may be applied to any suitable subject. In some embodiments, the subject is a mammalian subject. For example, the subject may be a mouse, rat, dog, cat, cow, sheep, horse or any other mammal of social, economic or research importance. Hence, the subject may be a mammal such as, for example, a human or a non-human mammal.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

The present invention will now be described with reference to specific examples, which should not be construed as in any way limiting.

EXAMPLES

Example 1

Effects of Monepantel (MPL) on Various Malignant and Non-Malignant Cell Lines

Materials and Methods

Cell Lines and Cell Culture

All cell lines described herein were purchased from ATCC. Cells were cultured according to the manufacturer's instructions in the media listed in Table 2 (below) and in 5% FBS. Cells were seeded in 96-well plates (2,000-3,000 cells/well) and culture overnight prior to treatment with MPL. Control cultures were treated with ethanol alone.

TABLE 2

| Tissue Cell Culture Media | | |
| --- | --- | --- |
| Tissue Origin | Cell Line/Cell Name | Media |
| Breast | MCF-7 | DMEM |
| Breast | MDA-MB-231 | DMEM |
| Breast | T47-D | DMEM |
| Cervical | HeLA | DMEM |
| Colorectal | HCT-116 | RPMI |
| Colorectal | HT-29 | RPMI |
| Colorectal | HT-29 5m11 | RPMI |
| Glial | LN-18 | DMEM |
| Glial | T98G | EMEM |
| Glial | U87 | EMEM |
| Glial | U251 | EMEM |
| Hepatic | HEP3B | RPMI |
| Mesenchymal | HT-1080 | EMEM |
| Mesenchymal | SW-872 | Leibovitz's L-15 Medium |
| Mesothelial | PET | RPMI |
| Mesothelial | REN | RPMI |
| Mesothelial | YOU | RPMI |
| Ovarian | 1A9 | RPMI |
| Ovarian | A2780 | RPMI |
| Ovarian | IGROV-1 | RPMI |
| Ovarian | OVCAR-3 | RPMI |
| Ovarian | SKOV-3 | RPMI |
| Pancreatic | ASPC-1 | RPMI |
| Pancreatic | CFPAC-1 | ISCOVE |
| Prostatic | DU-145 | EMEM |
| Prostatic | LNCaP | RPMI |
| Prostatic | PC-3 | RPMI |
| Epidermal | HaCat | DMEM |
| Mesenchymal | 3T3 (fibroblast) | DMEM |
| Nephritic | HEK | DMEM |
| Ovarian | CHO | DMEM |
| Endothelial | Endothelial | Lonza Endothelial Growth Medium |
| Glial | Glial | Gibco Astrocyte Medium |
| Ovarian | HOSE | Ovarian Epithelial Cell Medium (OEpiCM) |

Culture and Cytotoxicity Assay

Cytotoxicity was assessed using the sulforhodamine B (SRB) assay and reported as half maximal inhibitory concentration (IC50; Table 3). Cells were seeded in 96-well plates (2,000-3,000 cells/well), treated with the indicated compound(s) for 72 h, fixed, washed and stained with 100 μl of 0.4% (w/v) SRB dissolved in 1% acetic acid. Unbound dye was removed by five washes with 1% acetic acid before air-drying. Bound SRB was solubilized with 100 μl of 10 mM Tris base (pH 10.5) and the absorbance read at 570 nm.

Results

The Inventors have tested the addition of MPL (0, 5, 10, 25, 50 and 100 μmol/L) to cultures of: (i) 28 malignant, (ii) four immortalised, and (iii) three early or primary passage non-malignant and healthy cell populations, and assessed cytotoxicity using the SRB assay, as described above. Corresponding cytotoxicity of the major metabolite MPL-SO2 has also been tested where indicated. Malignant cell lines included: (i) breast [MCF-7, MDA-MB-231, T47-D], (ii) cervical [HeLa], (iii) colorectal [C170, HCT-116, HT-29, HT-295m11], (iv) glial [LN-18, T98G, U87, U251], (v) hepatic [Hep3B], (vi) mesenchymal (sarcoma): fibrosarcoma and liposarcoma [HT-1080, SW-876](vii) mesothelial [PET, YOU], (viii) ovarian [1A9, A2780, IGROV-1, OVCAR-3, SKOV-3], (ix) pancreatic [AsPC-1, CFPAC-1] and (x) prostatic [DU-145, LNCaP, PC-3]. Immortalised cell lines included: (i) epidermal [HaCat], (ii) mesenchymal [3T3](iii) nephritic [HEK], and (iv) ovarian [CHO]. Non-malignant primary/early passage cell types included: (i) endothelial [human umbilical vein endothelial cell; HUVEC], (ii) glial [human fetal astrocytes], and (iii) ovarian [human ovarian surface epithelial; HOSE]. HUVEC, human fetal astrocytes and HOSE cells are non-transformed, non-immortalized and non-malignant, freshly isolated/low passage number cell populations, from apparently healthy non-diseased tissue. These healthy cell populations were included in the experimental series as controls for non-specific toxicity. Both MPL and MPL-SO$_2$ were suspended in ethanol and applied in final concentrations of 0.5 to 1% ethanol in the respective culture media.

TABLE 3

The half maximal inhibitory concentration (IC50) of MPL and MPL-SO$_2$ for various malignant, immortalized and non-malignant cell lines.

| Cell Type | Tissue Origin | Cell Line/ Cell Name | IC50 μM | |
| --- | --- | --- | --- | --- |
| | | | Mpl | Mpl-SO$_2$ |
| Malignant | Breast | MCF-7 | 15.4 ± 1.1 | 8.0 ± 0.7 |
| Malignant | Breast | MDA-MB-231 | 25.8 ± 0.2 | 21.6 ± 7.5 |
| Malignant | Breast | T47-D | 5.3 ± 0.0 | 10.2 ± 0.6 |
| Malignant | Cervical | HeLA | 15.8 ± 0.3 | 18.2 ± 2.6 |
| Malignant | Colorectal | C170 | ~20 | |
| Malignant | Colorectal | HCT-116 | 10.5 ± 0.0 | 22.5 ± 5.7 |

TABLE 3-continued

The half maximal inhibitory concentration (IC50) of MPL and MPL-SO$_2$ for various malignant, immortalized and non-malignant cell lines.

| Cell Type | Tissue Origin | Cell Line/ Cell Name | IC50 μM Mpl | Mpl-SO$_2$ |
|---|---|---|---|---|
| Malignant | Colorectal | HT-29 | 5.9 ± 0.2 | 2.8 ± 0.7 |
| Malignant | Colorectal | HT-29 5m11 | 10.4 ± 0.0 | 21.7 ± 0.0 |
| Malignant | Glial | LN-18 | 9.4 ± 0.8 | 6.6 ± 0.7 |
| Malignant | Glial | T98G | 18.2 ± 0.6 | 25.4 ± 0.3 |
| Malignant | Glial | U87 | 18.0 ± 7.1 | 20.5 ± 1.9 |
| Malignant | Glial | U251 | 17.0 ± 1.2 | |
| Malignant | Hepatic | Hep3B | 15.8 ± 0.0 | |
| Malignant | Mesenchymal | HT-1080 (Fibrosarcoma) | 17.2 ± 0.0 | |
| Malignant | Mesenchymal | SW-872 (Liposarcoma) | 14.7 ± 0.0 | |
| Malignant | Mesothelial | PET | 26.0 ± 0.0 | |
| Malignant | Mesothelial | REN | 2.5 ± 0.2 | |
| Malignant | Mesothelial | YOU | 23.0 ± 0.0 | |
| Malignant | Ovarian | 1A9 | 2.5 ± 0.5 | 3.4 ± 0.1 |
| Malignant | Ovarian | A2780 | 10.0 ± 3.8 | 4.2 ± 2.1 |
| Malignant | Ovarian | IGROV-1 | 4.4 ± 0.3 | 4.4 ± 1.5 |
| Malignant | Ovarian | OVCAR-3 | 6.3 ± 0.8 | 5.5 ± 1.3 |
| Malignant | Ovarian | SKOV-3 | 31.2 ± 0.8 | 26 ± 0.0 |
| Malignant | Pancreatic | AsPC1 | 7.2 ± 0.3 | |
| Malignant | Pancreatic | CFPAC-1 | 30.1 ± 5.5 | |
| Malignant | Prostatic | DU-145 | 23.0 ± 0.0 | |
| Malignant | Prostatic | LNCaP | 7.3 ± 0.0 | |
| Malignant | Prostatic | PC-3 | 21.0 ± 0.0 | |
| Immortalised | Epidermal | HaCat | 21.2 ± 3.2 | 42.7 ± 8.0 |
| Immortalised | Mesenchymal | 3T3 (fibroblast) | 12.4 ± 0.4 | 11.2 ± 1.1 |
| Immortalised | Nephritic | HEK | 34.6 ± 0.9 | |
| Immortalised | Ovarian | CHO | 34.6 ± 0.8 | 73.7 ± 6.9 |
| Non-malignant | Endothelial | HUVEC | 87.0 ± 0.0 | 47.0 ± 0.0 |
| Non-malignant | Glial | Human Fetal Astrocytes | 85.6 ± 2.7 | |
| Non-malignant | Ovarian | HOSE | >100 | |

MPL displayed a selective and relatively high cytotoxic effect upon all 28 malignant cell lines tested, with the exception of the pancreatic CFPAC-1 and the p53-mutant and chemoresistant ovarian SKOV-3 cell line which were slightly less sensitive, (2 μM<IC50 proliferation <25 μM; Table 3). All immortalized cell lines and the CFPAC-1 and SKOV-3 cell lines displayed an intermediate sensitivity to MPL (12 μM <IC50 proliferation <35 μM; Table 3). In contrast, the three early/primary passage cell populations: HUVEC, human fetal astrocytes and HOSE cells, all displayed a relatively low sensitivity to MPL (IC50 proliferation >85 μM; Table 3). The cytotoxicity of MPL-SO$_2$ to all cell lines and cells tested in this series of experiments was generally comparable to the parent compound, MPL.

Example 2

Effects of Pharmaceutical Combination of Monepantel (MPL) and Other Anticancer Compounds in Ovarian Cancer Cell Lines Materials and Methods Cell Lines The human ovarian cancer cell lines OVCAR-3 and A2780, and the normal non-malignant human ovarian surface epithelial (HOSE) cell line, were all obtained from the American Type Culture Collection (ATCC) and maintained according to their instructions.

Viability and Proliferation Assays

In order to evaluate the effect of MPL on the in vitro efficacy of an established drug was evaluated using cell viability and cell proliferation assays. Cell viability was conducted according to standard Trypan Blue method. Cell proliferation was assessed using the sulforhodamine B (SRB) assay. For viability experiments, cells were seeded in 6 well plates, whereas for proliferation assays cells were grown in 96 well plates. Following over-night attachment, cells were treated with the intended drug at various concentrations either alone or in combination with monepantel (MPL) for 72 h. Parallel to this, cells treated with MPL alone were also deployed for comparative purposes. Following incubation for 72 h in a standard cell culture incubator, effect of mono and combined drug treatments on cell viability and/or cell proliferation was assessed through using Trypan Blue or SRB assays respectively.

For viability assay, at the end of treatment period, cells were washed with PBS, trypsinized and counted using Trypan blue and hemocytometer. For the SRB assay cells were fixed, washed and stained with 100 μl of 0.4% (w/v) SRB dissolved in 1% acetic acid. Unbound dye was removed by five washes with 1% acetic acid before air drying. Bound SRB was solubilized with 100 μl of 10 mM Tris base (pH 10.5) and the absorbance read at 570 nm. Monepantel (gift by Novartis, Basel, Switzerland) was dissolved in 100% ethanol and then diluted with the cell culture media. Other agents employed in the study were purchased either from Sigma Australia or Sapphire Australia, prepared and preserved for cell culture use according to supplier instructions.

Statistical Analysis

All data are reported as the mean±standard errors (S.E.M.) from at least two independent experiments. Differences in cell proliferation between MPL treated versus control group were analyzed using one way ANOVA with Tukey's multiple comparison test.

Results

TABLE 4

Pharmaceutical combination of monepantel (MPL) and other anticancer compounds in OVCAR-3 CELL

| No. | Pharmaceutical combination | Concentration (μM) and duration | Synergistic effect |
|---|---|---|---|
| 1 | minocycline and MPL | minocycline: 10 μM<br>MPL: 5, 25 μM<br>72 hours | Yes |
| 2 | albendazole and MPL | albendazole: 0.1 μM<br>MPL: 5, 10 μM<br>72 hours | Yes |
| 3 | albendazole and MPL | albendazole: 0.25 μM<br>MPL: 5, 25 μM<br>72 hours | Yes |
| 29 | albendazole and MPL | albendazole: 0.1 μM<br>MPL: 2.5 μM<br>72 hours | Yes |
| 4 | levamisole and MPL | levamisole: 10 μM<br>MPL: 5, 25 μM<br>72 hours | Yes |
| 7 | glibenclamide and MPL | glibenclamide: 10 μM<br>MPL: 10 μM<br>72 hours | Yes |
| 8 | trifluoperazine and MPL | trifluoperazine: 10, 100 μM<br>MPL: 10 μM<br>72 hours | Yes |
| 9 | amiloride and MPL | amiloride: 10, 100 μM<br>MPL: 10 μM<br>72 hours | Yes |

TABLE 4-continued

Pharmaceutical combination of monepantel (MPL) and other anticancer compounds in OVCAR-3 CELL

| No. | Pharmaceutical combination | Concentration (μM) and duration | Synergistic effect |
|---|---|---|---|
| 11 | flutamide and MPL | flutamide: 1 μM<br>MPL: 10 μM<br>48 hours | Yes |
| 12 | serotonin and MPL | serotonin: 100 μM<br>MPL: 10 μM<br>48 hours | Yes |
| 13 | tamoxifen and MPL | tamoxifen: 0.5 μM<br>MPL: 10 μM<br>48 hours | Yes |
| 19 | tamoxifen and MPL | tamoxifen: 0.5, 1, 5, 10 μM<br>MPL: 5 μM<br>72 hours | Yes |
| 23 | tamoxifen and MPL | tamoxifen: 1 μM<br>MPL: 2.5 μM<br>72 hours | Yes |
| 14 | wortmannin and MPL | wortmannin: 0.1 μM<br>MPL: 10 μM<br>48 hours | Yes |
| 15 | adenosine triphosphate (ATP) and MPL | ATP: 100 nM<br>MPL: 5 μM<br>72 hours | Yes |
| 16 | clozapine and MPL | clozapine: 1, 10 μM<br>MPL: 5 μM<br>72 hours | Yes |
| 18 | vitamin E and MPL | vitamin E: 100, 200 μG<br>MPL: 5 μM<br>72 hours | Yes |
| 21 | zinc chloride and MPL | zinc chloride: 5, 50 μM<br>MPL: 2.5 μM<br>72 hours | Yes |
| 30 | mifepristone and MPL | mifepristone: 1, 10 nM<br>MPL: 2.5 μM<br>72 hours | Yes |

TABLE 5

Pharmaceutical combination of monepantel (MPL) and other compounds in OVCAR-3 CELL - Comparative Examples

| No. | Pharmaceutical combination | Concentration (μM) and duration | Synergistic effect |
|---|---|---|---|
| 5 | mecamylamine and MPL | mecamylamine: 10, 100 μM<br>MPL: 5, 10, 25, 50 μM<br>72 hours | No effect |
| 6 | verapamil and MPL | verapamil: 5, 10, 25 μM<br>MPL: 10 μM<br>72 hours | No effect |
| 10 | enalapril and MPL | enalapril: 10, 100 μM<br>MPL: 10 μM<br>72 hours | No effect |
| 17 | chloroquine and MPL | chloroquine: 1, 10 μM<br>MPL: 5 μM<br>72 hours | No effect |
| 20 | captopril and MPL | captopril: 10 μM<br>MPL: 5 μM<br>72 hours | No effect |
| 22 | glucose and MPL | glucose: 0.1, 1 mg/ml<br>MPL: 2.5 μM<br>72 hours | No effect |
| 24 | L-histidine and MPL | L-histidine: 100, 500 μM<br>MPL: 10 μM<br>24 hours | No effect |
| 25 | L-glutamine and MPL | L-glutamine: 100, 500 μM<br>MPL: 10 μM<br>24 hours | No effect |
| 26 | zinc chloride and MPL | zinc chloride: 5, 50 μM<br>MPL: 10 μM<br>24 hours | No effect |
| 27 | B-estradiol and MPL | B-estradiol: 0.01, 0.1, 0.5, 1 μM<br>MPL: 2.5 μM<br>72 hours | No effect |
| 28 | clozapine and MPL | clozapine: 0.5 μM<br>MPL: 2.5 μM<br>72 hours | No effect |
| 31 | dihydrotestosterone (DHT) and MPL | DHT: 5, 10, 50, 100 nM<br>MPL: 2.5 μM | No effect |

The data from doxorubicin are particularly impressive with the cytotoxicity being enhanced 100 fold.

Figure 22:
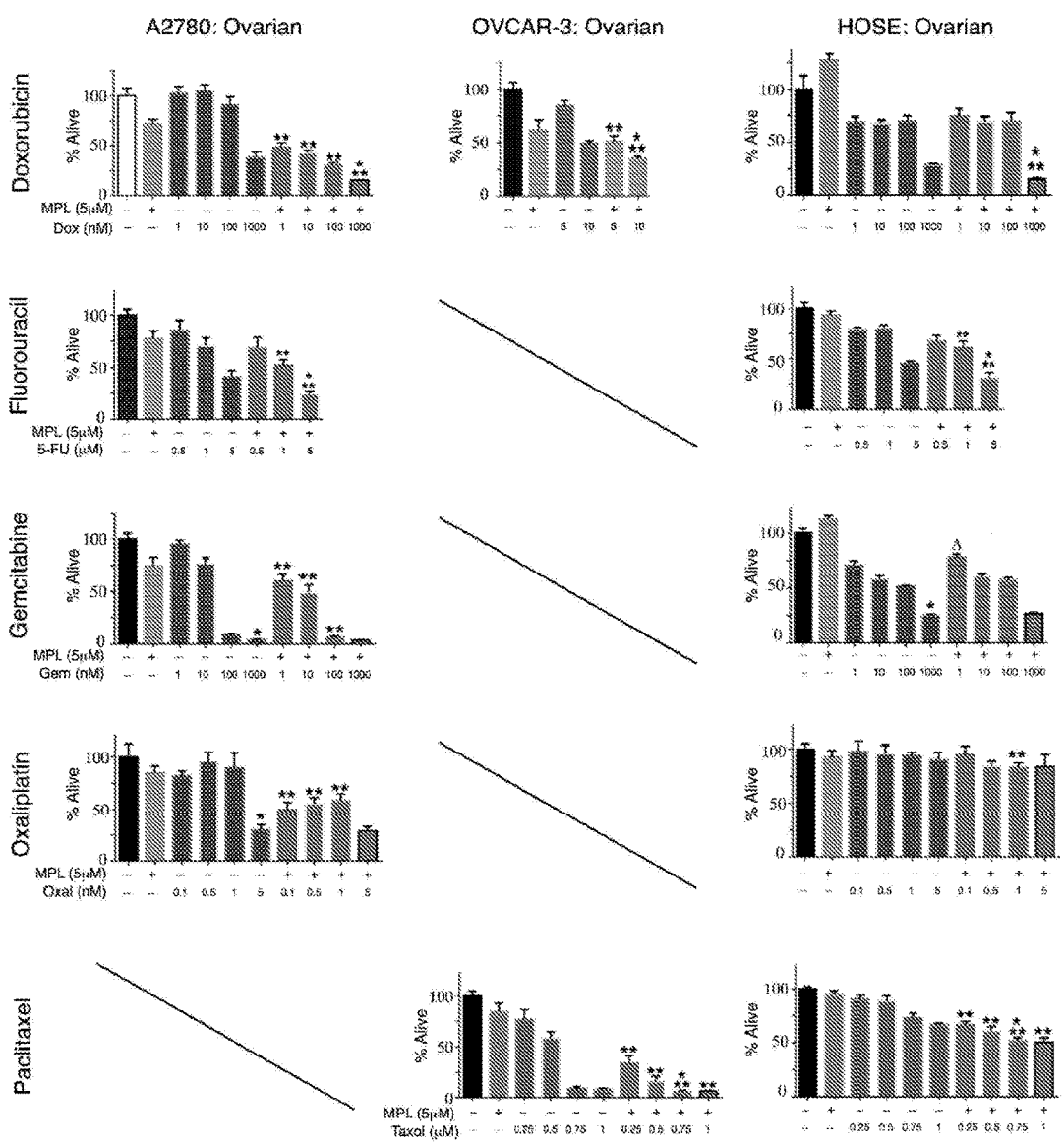
FIG. 22 shows interactions of MPL and doxorubicin, fluorouracil, gemcitabine, oxaliplatin or paclitaxel upon A2780 and OVCAR-3 malignant cells and HOSE non-malignant cells.

FIGS. 1 and 22 show that there is synergy between MPL and doxorubicin, and especially at lower concentrations of doxorubicin. This is important because of doxorubicin toxicity in man which limits dosage.

Figure 2:
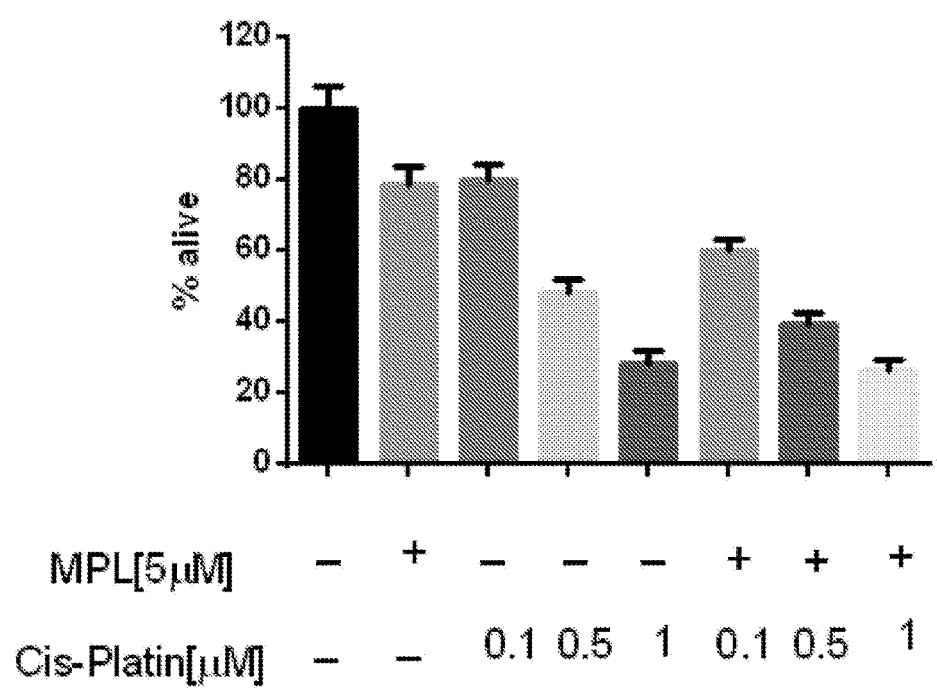
FIG. 2 shows an SRB assay of the treatment of A2780 cells for 72 hours with MPL and cisplatin.

FIG. 2 shows some increase of effect of cisplatin by addition of very low dose of MPL (DNA cross linker produces apoptosis).

FIG. 22 also shows a significant increase in the effect of 5 FU with MPL (anti-metabolite, irreversible inhibition of thymidylate synthase) as well as for the combination of tamoxifen/MPL. At low doses of gemcitabine, the combination of MPU gemcitabine shows a notable increase in efficacy of gemcitabine (gemcitabine is a nucleotide reductase inhibitor and is used to treat pancreatic, lung and other cancers).

Figure 3:
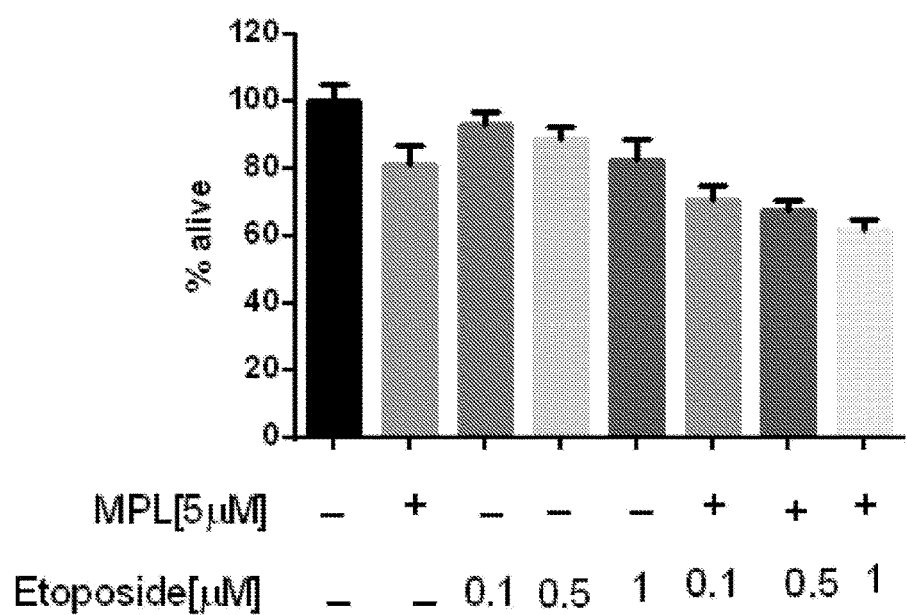
FIG. 3 shows an SRB assay of the treatment of A2780 cells for 72 hours with MPL and etoposide.

FIG. 3 shows some synergistic effect between etoposide and MPL.

Figure 4:
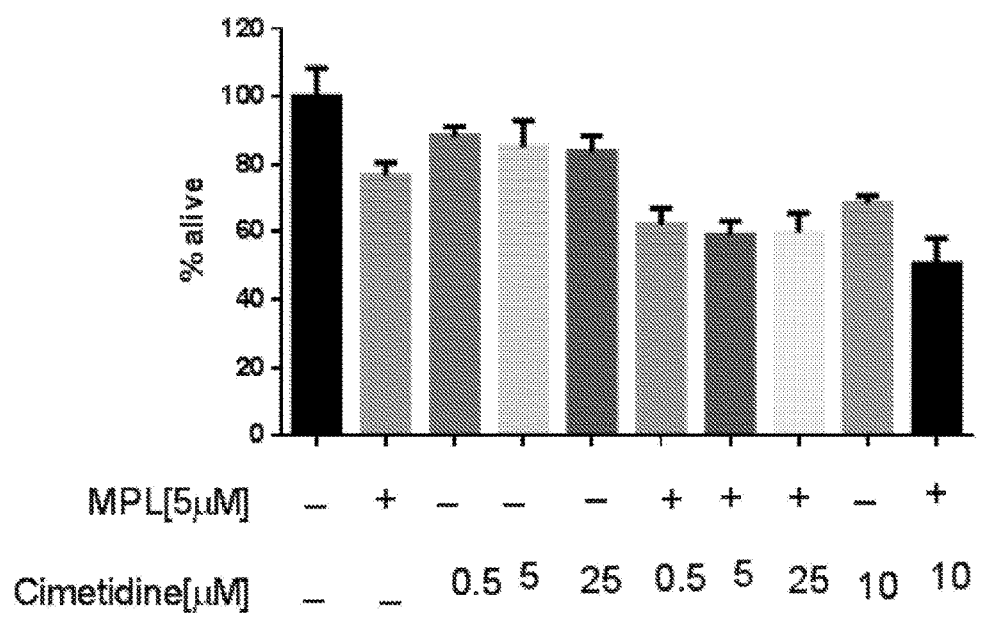
FIG. 4 shows an SRB assay of the treatment of A2780 cells for 72 hours with MPL and cimetidine.
Figure 5:
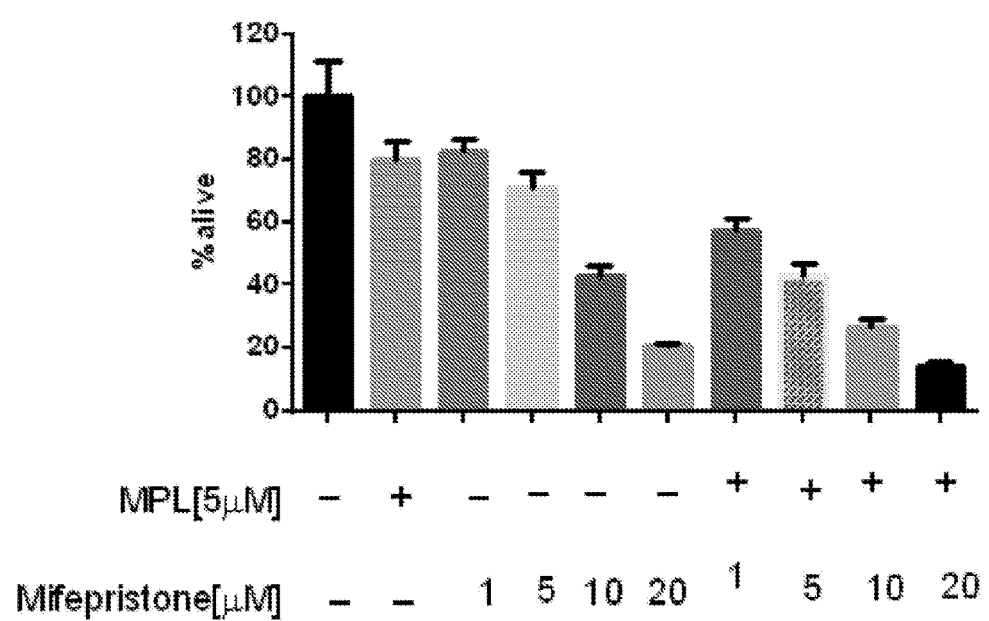
FIG. 5 shows an SRB assay of the treatment of A2780 cells for 72 hours with MPL and mifepristone.
Figure 6:
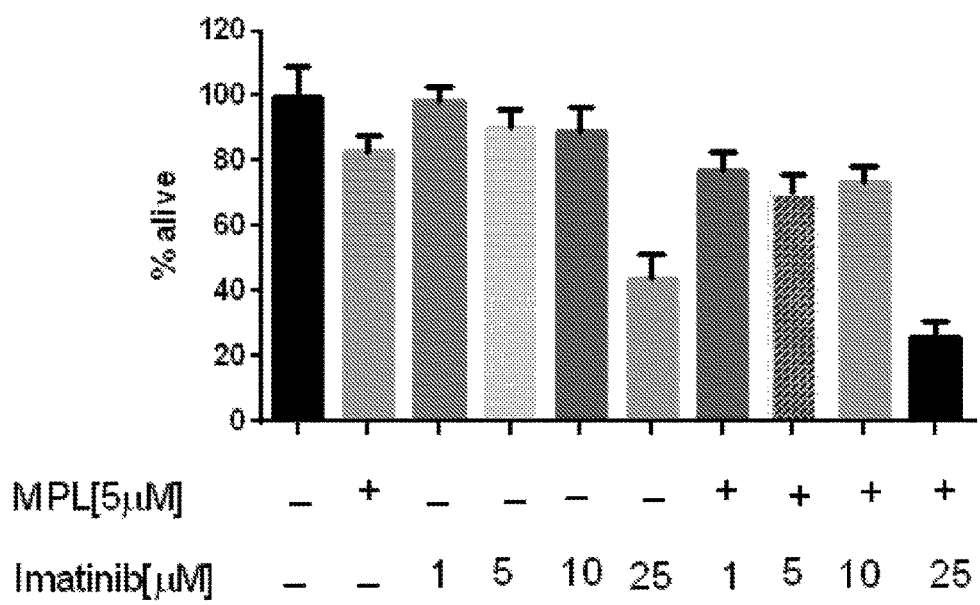
FIG. 6 shows an SRB assay of the treatment of A2780 cells for 72 hours with MPL and imatinib.
Figure 7:
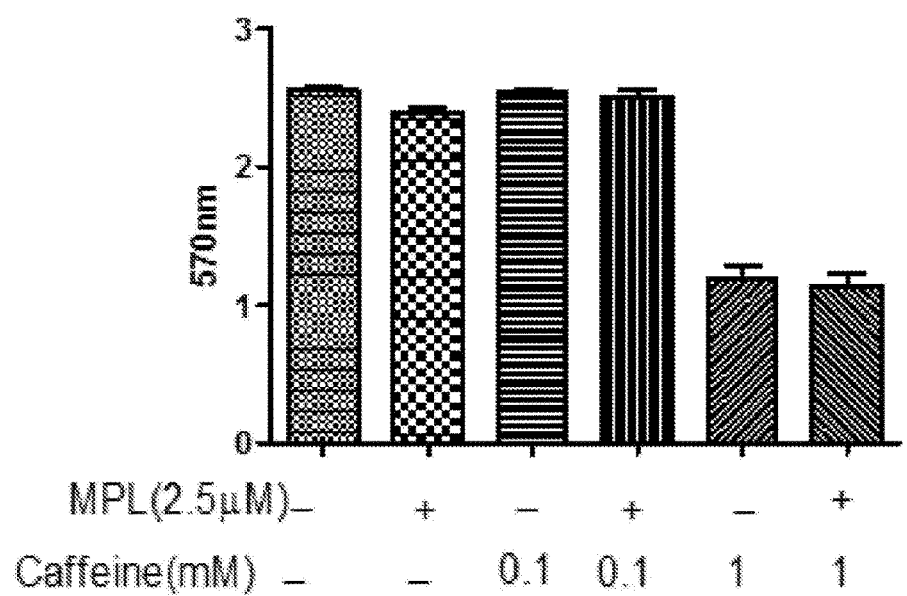
FIG. 7 shows an SRB assay of the treatment of OVCAR-3 cells for 72 hours with MPL and caffeine.
Figure 8:
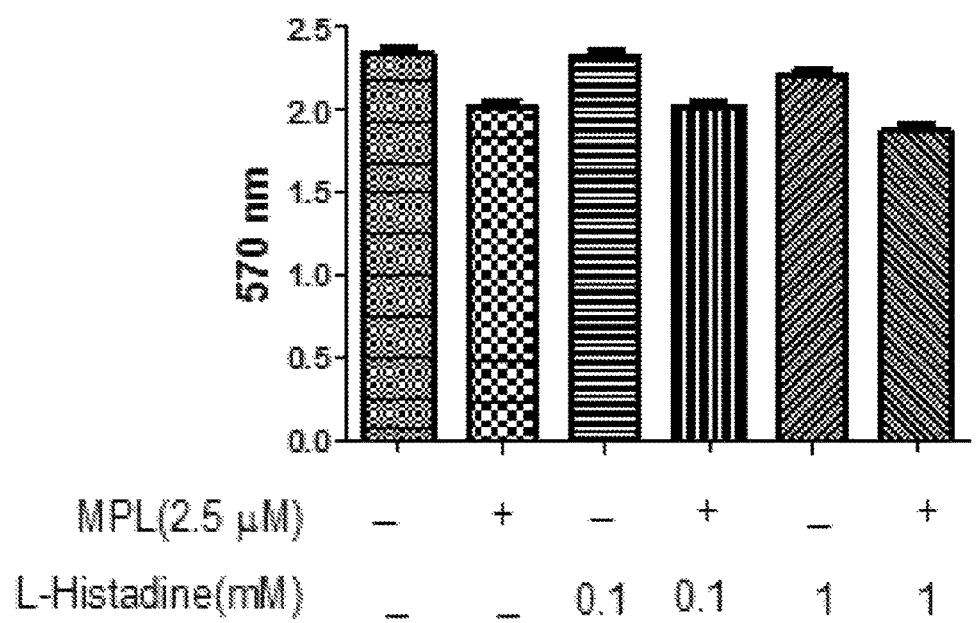
FIG. 8 shows an SRB assay of the treatment of OVCAR-3 cells for 72 hours with MPL and L-histidine.
Figure 9:
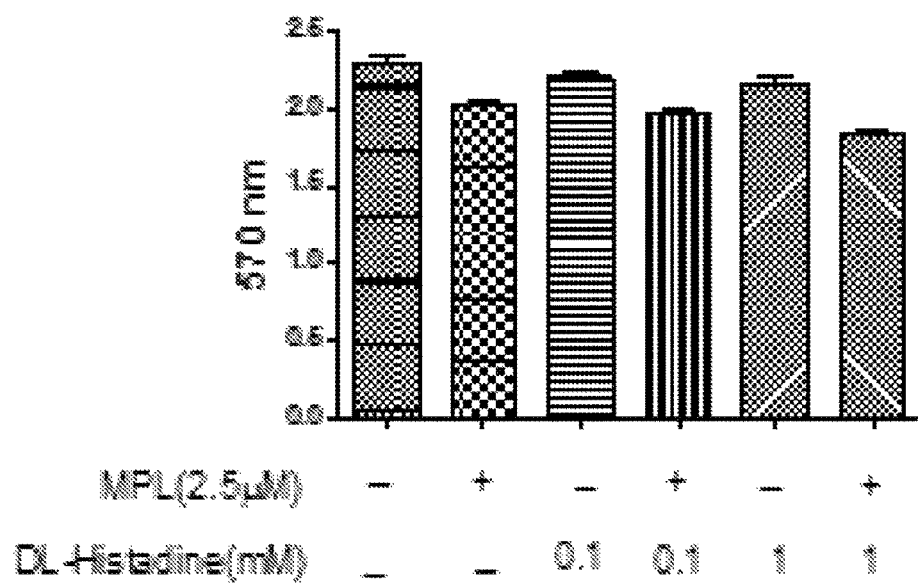
FIG. 9 shows an SRB assays of the treatment of OVCAR-3 cells for 72 hours with MPL and DL-histidine.
Figure 10:
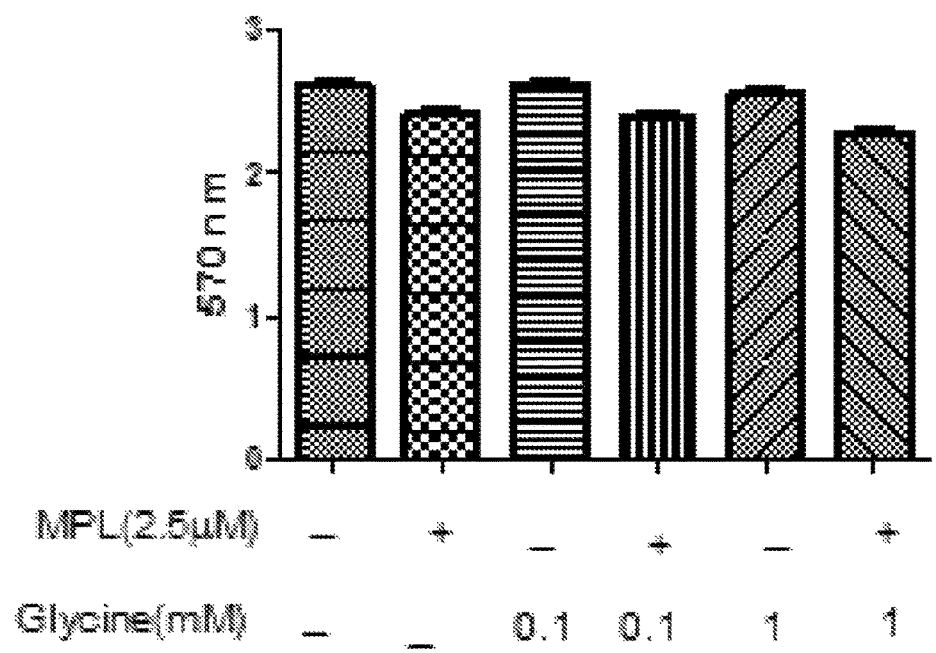
FIG. 10 shows an SRB assay of the treatment of OVCAR-3 cells for 72 hours with MPL and glycine hydrochloride.

FIGS. 4 to 6 show a significant combination synergistic effect of cimetidine with MPL, mifepristone with MPL and imatinib with MPL.

Figure 11:
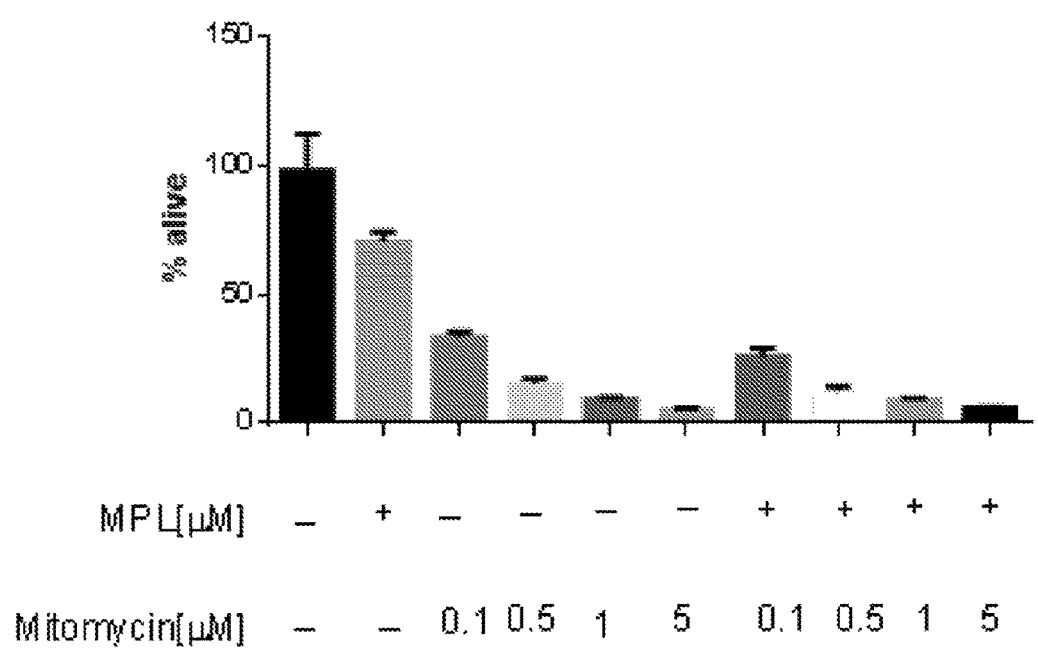
FIG. 11 shows an SRB assay of the treatment of A2780 cells for 72 hours with MPL and mitomycin.

FIG. 11 shows that the combination of mitomycin C with MPL results in effective enhancement of mitomycin C activity.

Figure 12:
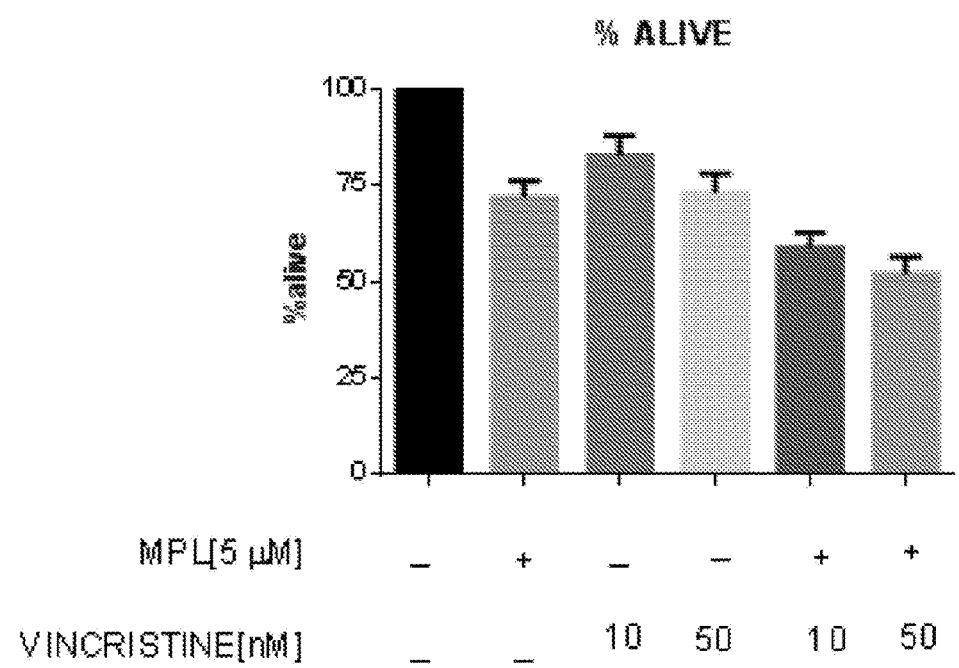
FIG. 12 shows an SRB assay of the treatment of A2780 cells for 72 hours with MPL and vincristine.

FIG. 12 shows a synergistic effect is exhibited with the combination of vincristine/MPL.

Figure 14:
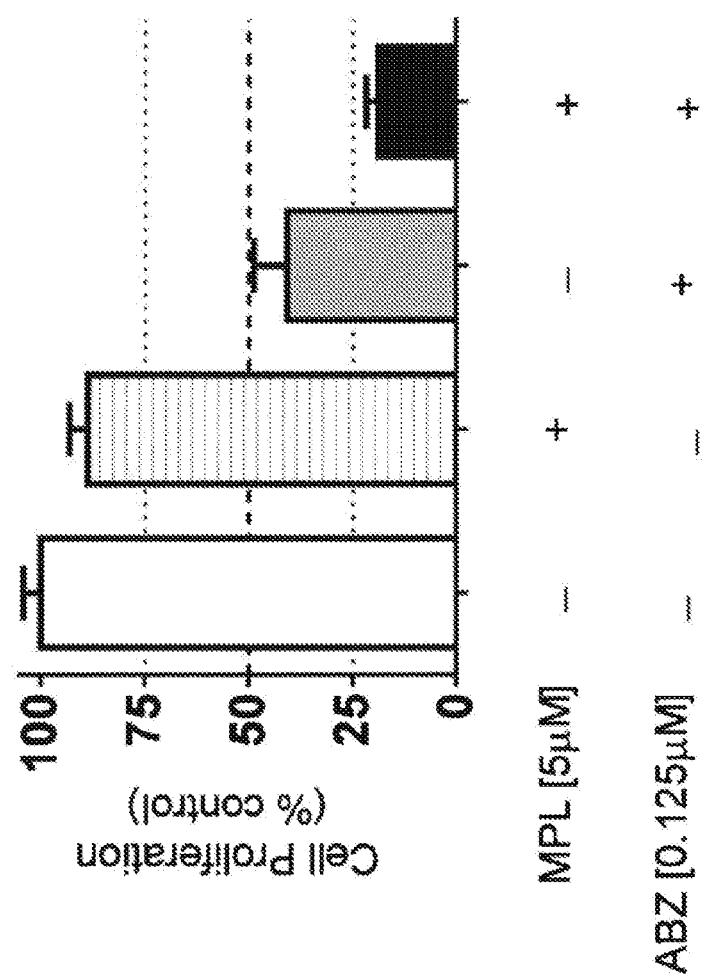
FIG. 14 shows A2780 cells (72 hour treatment) with MPL and albendazole (ABZ).

FIG. 14 shows that the combination of albendazole/MPL shows a good synergistic effect (albendazole is a benzimidazole carbamate which has been shown to have a variety of anticancer effects).

Figure 15:
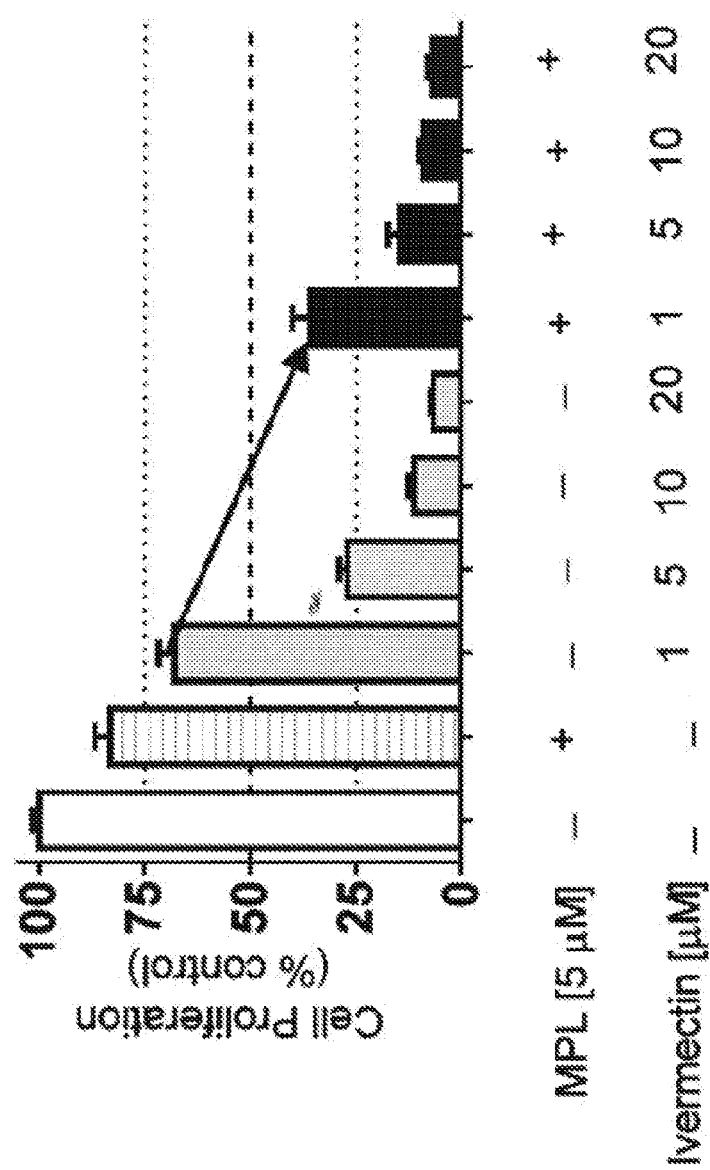
FIG. 15 shows A2780 cells (72 hour treatment) with MPL and ivermectin.

FIG. 15 shows that the combination of ivermectin/MPL showed a synergistic effect. Although the effects of ivermectin in treating cancer are largely unknown, ivermectin inhibited A2780 (ovarian).

Figure 16:
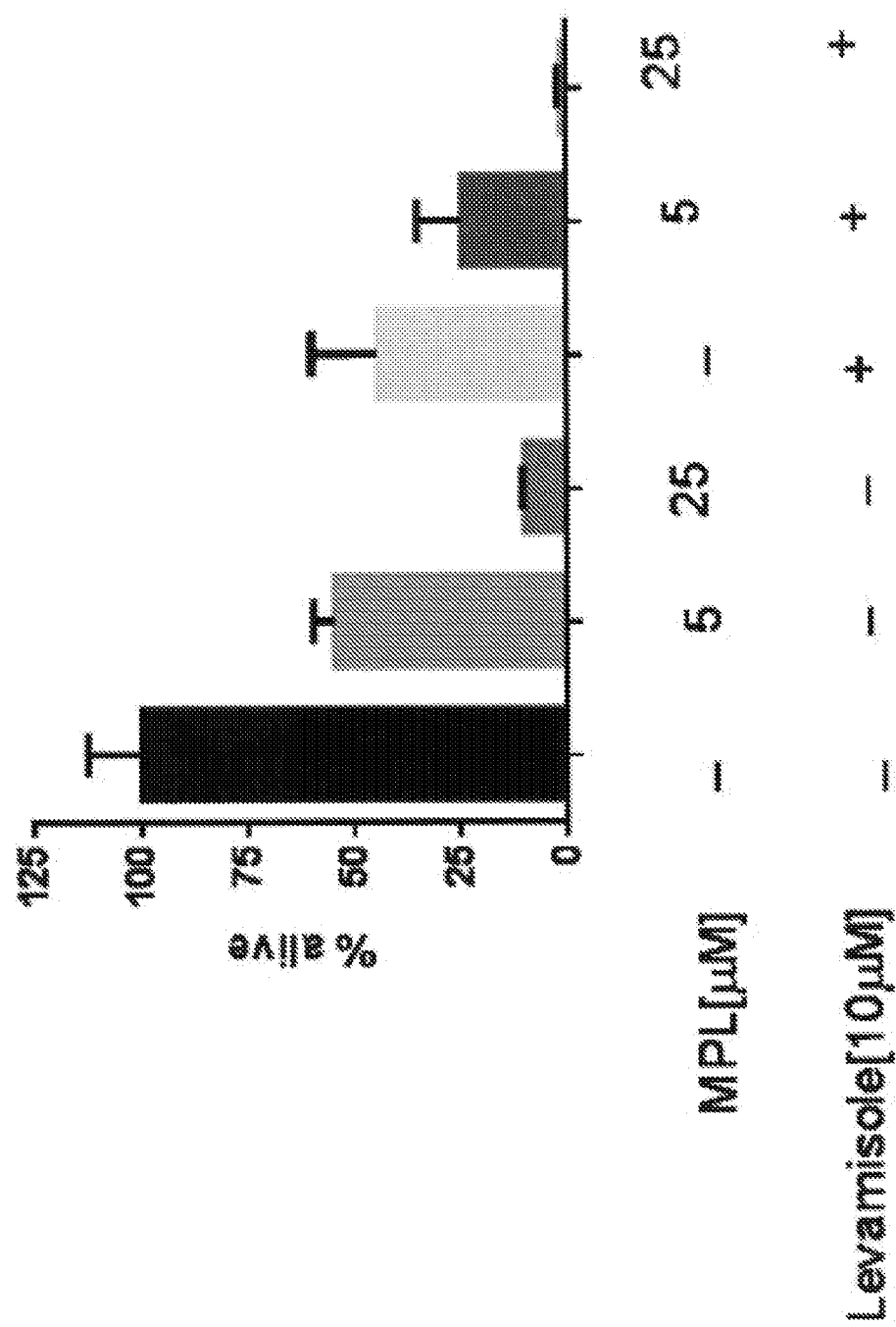
FIG. 16 shows OVCAR-3 (72 hour treatment) with MPL and levamisole.
Figure 17:
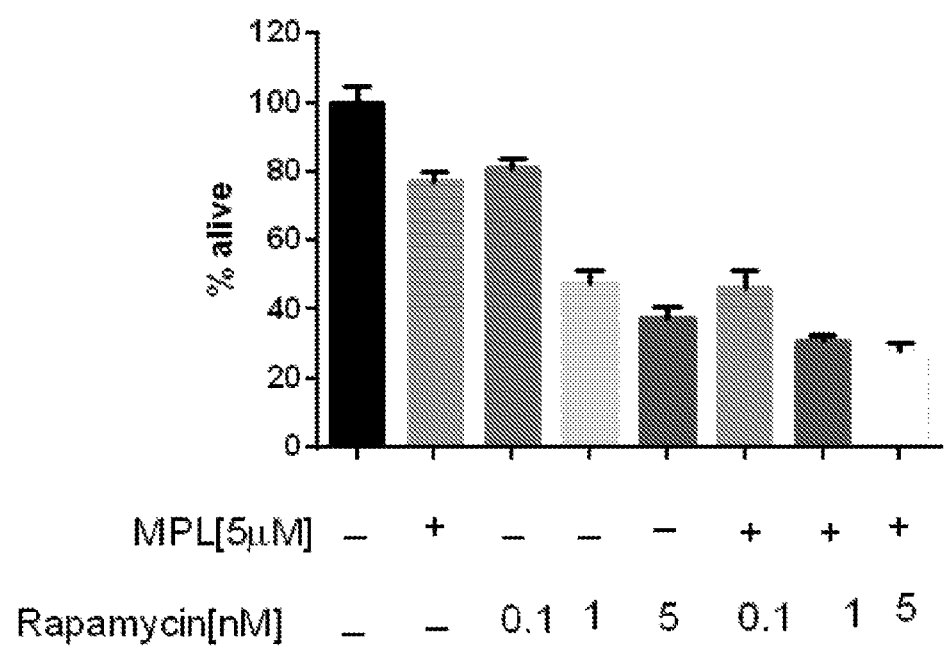
FIG. 17 shows an SRB assay of the treatment of A2780 cells (72 hour treatment) with MPL and rapamycin.
Figure 18:
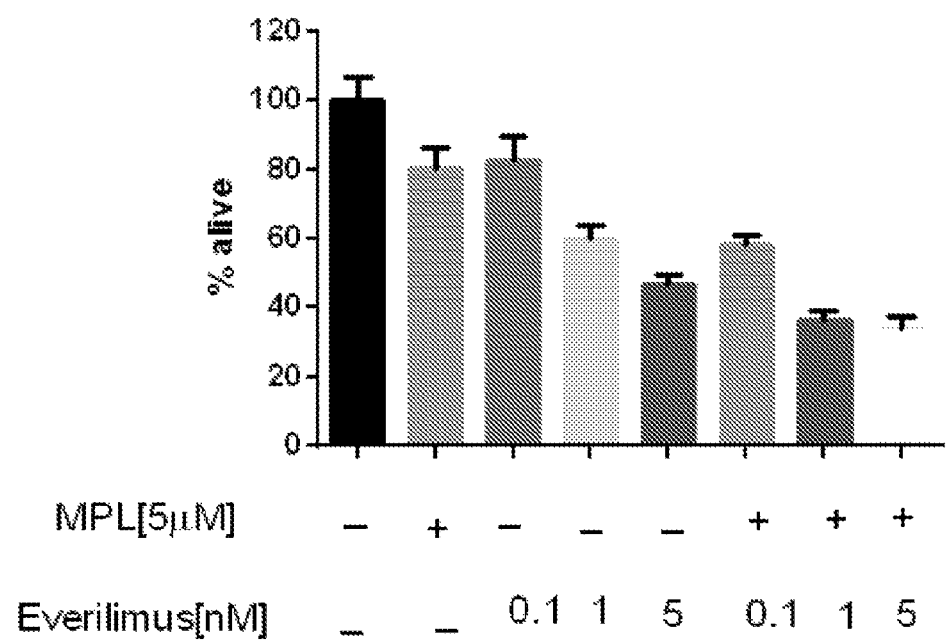
FIG. 18 shows an SRB assay of the treatment of A2780 cells (72 hour treatment) with MPL and everilimus.
Figure 19:
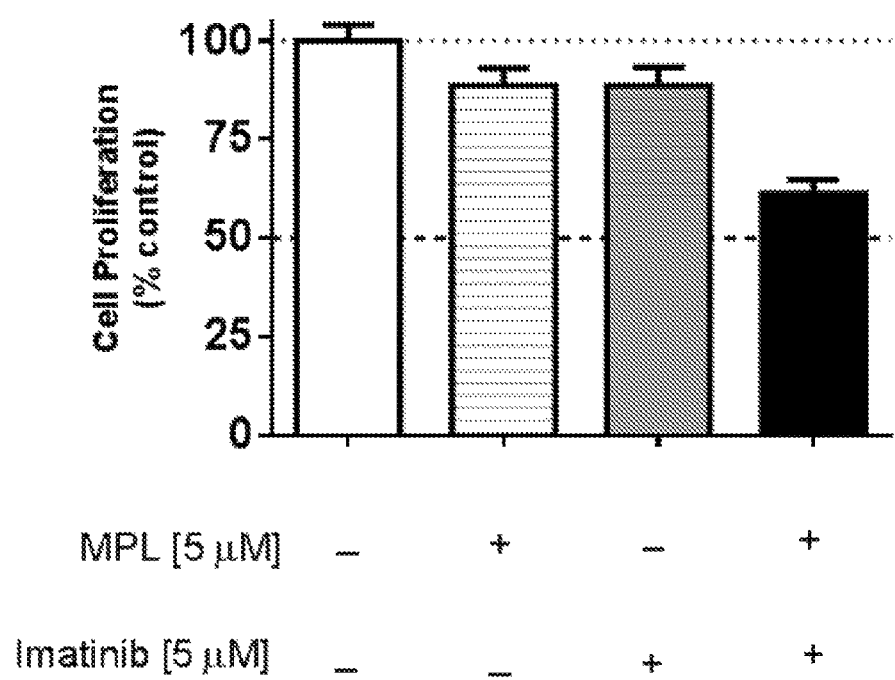
FIG. 19 shows A2780 cells (72 hour treatment) with MPL and imatinib.
Figure 26:
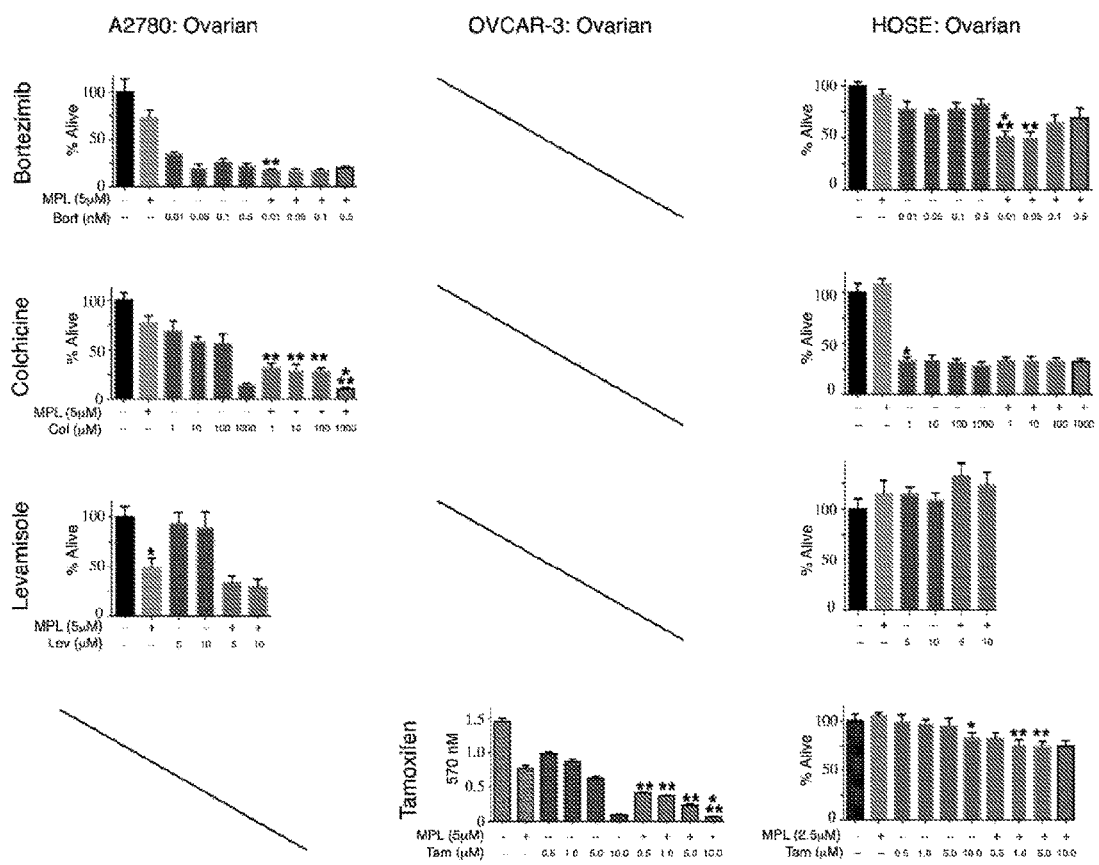
FIG. 26 shows interactions of MPL and bortezimib, colchicine, levamisole or tamoxifen upon A2780 and OVCAR-3 malignant cells and HOSE non-malignant cells.

FIG. 16 shows a significant synergistic effect of MPL with levamisole in OVCAR-3 cells FIG. 26 shows a synergistic effect of MPL with colchicine.

MPL has no effect on the activity of glycine, L-histidine or DL-histidine.

FIGS. 7 to 10 show that the combinations of caffeine/MPL, histidine/MP, DL histidine/MPL and glycine/MPL show no synergistic effect.

Figure 13:
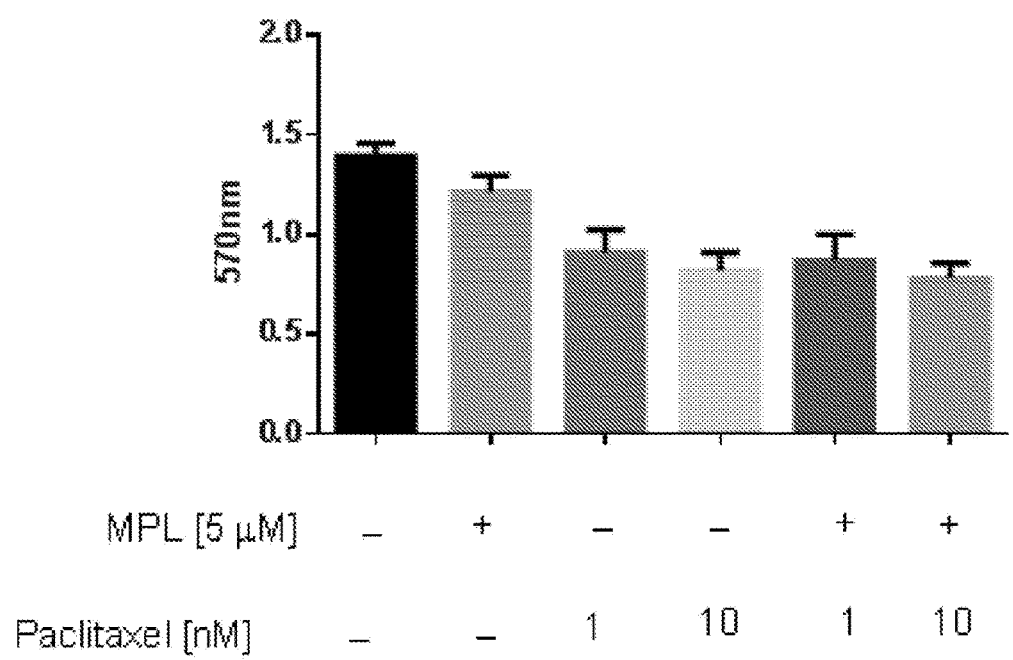
FIG. 13 shows an SRB assay of the treatment of A2780 cells for 72 hours with MPL and paclitaxel.

FIG. 13 shows that the combination of paclitaxel/MPL shows no synergistic effect when administered to A2780 cells. However, as depicted in FIG. 22, a synergistic inhibition was observed for both OVCAR-3 and non-malignant HOSE cells.

Example 3

Effects of Pharmaceutical Combination of Monepantel (MPL) in Double Combination with Various First and Second Line Standard-of-care Chemotherapeutic Drugs The inventors have tested MPL in double combination with various first and second line standard-of-care chemotherapeutic drugs for synergistic interaction upon malignant cell cytotoxicity using the SRB assay

Materials and Methods

Cell lines were all obtained from the American Type Culture Collection (ATCC) and maintained as outlined in Example 1 above. The cytotoxicity assays were also performed as outlined in Example 1 above.

Statistical Analysis

All data are reported as the mean±standard errors (S.E.M.) from at least two independent experiments. Differences in cell proliferation between MPL treated versus control group were analyzed using one way ANOVA with Tukey's multiple comparison test.

Results

The Inventors have tested the addition of eight drugs at a range of concentrations in combination with MPL, including: cisplatin, doxorubicin, fluorouracil, flutamide, gemcitabine, minocycline, oxaliplatin and paclitaxel. Malignant cell lines tested to date include the human: LN18 and U87 glioblastoma; Hep3B hepatoma; PET, REN and YOU mesothelioma; AsPC-1 and CFPAC-1 pancreatic adenocarcinoma; A2780 and OVCAR-3 ovarian carcinoma and adenocarcinoma, respectively; and LNCaP prostate malignant, derived cell lines. It is considered that any future clinical application of MPL would involve systemic administration and with this in mind, non-malignant and healthy HOSE cells have been included as a cytotoxicity control for each of these combinations. Supplementary data obtained using minocycline and tamoxifen in more restricted tests (less comprehensive concentration ranges) are described in Example 4, below. C170 and HT29 colorectal cells and SKOV-1 ovarian cells have also been assessed in more restricted tests (less comprehensive drug concentration ranges) and are also described in Example 4, below.

Cell lines/name used versus the drug combination. Treatment was with 5 μM MPL and the drug combination for 72 h, apart from Hep3B cells where treatment was for 48 h. Corresponding HOSE 48 h treatment times are indicated in FIG. 24. In the "Combined Drug" columns, a ✓ indicates synergistic inhibition, while an ✗ indicates no synergistic effect). [1]x=number of events, X=number of experiments. [2]In one experiment (Oxaliplatin) a Tukey post-hoc test gave p>0.05, but a Newman-Keuls post-hoc test gave p<0.05. [3]HOSE control cells were generally insensitive to the administration of MPL, however, in two experiments cytotoxicity was recorded at low levels: 5 and 3%, respectively (oxaliplatin and flutamide experiments, see FIGS. 21 and 22, below). [4]Synergy was observed upon HOSE cells only at high MPL concentrations (see FIG. 22 below). [5]Synergy upon HOSE cells resulted in a modest decrease in HOSE cell survival (see FIG. 22 below). [6]No synergistic effect upon HOSE cells was observed after 48 of treatment: cytotoxicity observed after this time was only attributable to the effects of the Combined Drug (see FIG. 23 below).

Figure 20:
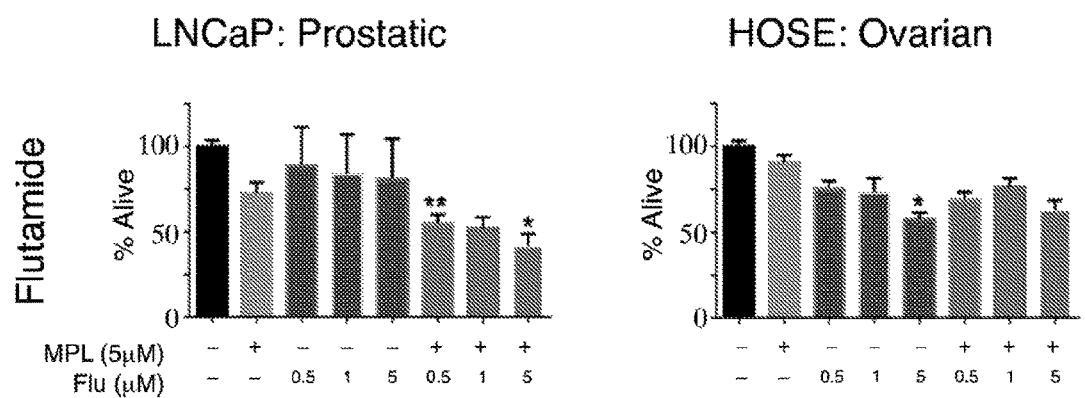
FIG. 20 shows interactions of MPL and flutamide upon LNCAP-1 malignant cells and HOSE non-malignant cells.

In FIG. 20, MPL and flutamide display a synergistic interaction upon LNCAP-1 cells, but not HOSE cells at the concentrations tested. * indicates the most effective dose of all doses tested whether the drug was used alone or in combination. The most effective dose provided the highest cytotoxic effect at the lowest drug concentration tested. ** indicates synergy.

Figure 21:
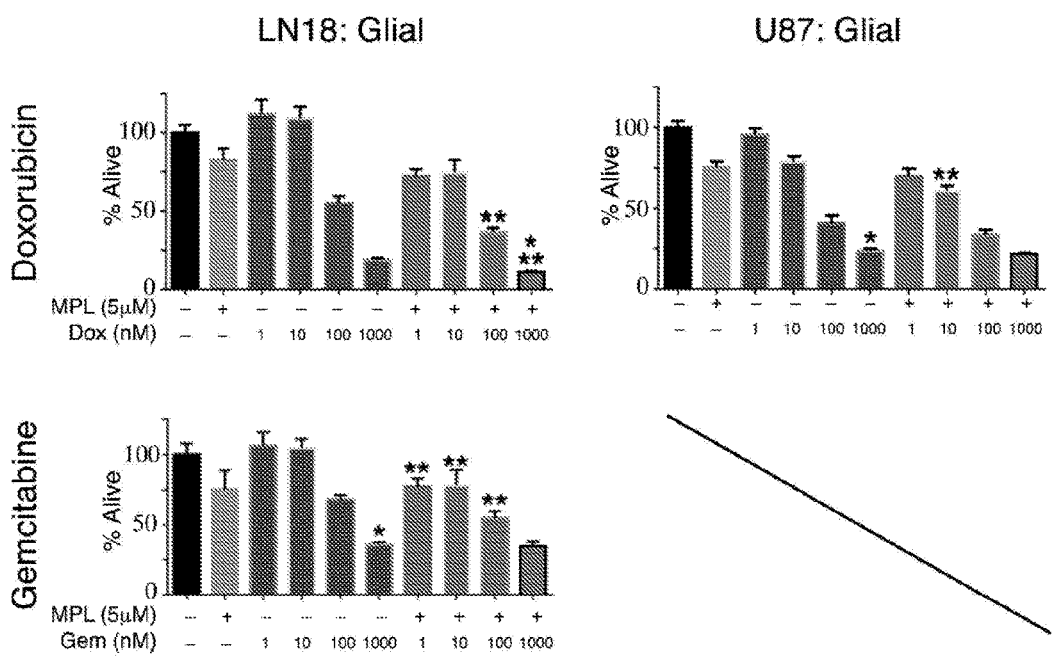
FIG. 21 shows interactions of MPL and doxorubicin or gemcitabine upon LN18 and U87 malignant cells.

In FIG. 21, MPL and doxorubicin display a synergistic interaction upon LN18 and U87 glial cells. MPL and gemcitabine display a synergistic interaction upon LN18 cells. * indicates the most effective dose, ** indicates synergy.

In FIG. 22 MPL and doxorubicin display a synergistic interaction upon A2780 and OVCAR cells at low doxorubicin concentrations, and A2780, OVCAR and HOSE control cells at high doxorubicin concentrations. MPL and fluorouracil display a synergistic interaction upon both A2780 malignant and HOSE control cells. Gemcitabine and MPL display a strong synergistic interaction upon A2780 cells and do not display the same synergistic interaction upon HOSE control cells. MPL and oxaliplatin display a strong synergistic interaction upon A2780 cells and a relatively small yet synergistic interaction upon HOSE control cells. MPL and paclitaxel display a synergistic interaction upon OVCAR-3 and HOSE cells. MPL alone displays a small but significant cytotoxic effect upon HOSE cells in Rows 2 (fluorouracil) and 5 (paclitaxel) (not indicated). * indicates the most effective dose, ** indicates synergy, A indicates a cytoprotective effect.

TABLE 6

Synergistic cytotoxicity elicited between MPL and selected cytotoxic drugs on malignant cell lines in vitro.

| | Mpl Alone | Combined Drug | | | | | | |
|---|---|---|---|---|---|---|---|---|
| Cell Line/Name | Mpl (x/X)[2] Inhibition | Cisplatin (Cis) | Doxorubicin (Dox) | Fluorouracil (5-FU) | Flutamide (Flu) | Gemcitabine (Gem) | Oxaliplatin (Oxal) | Paclitaxel (Taxol) |
| LN18 Glioblastoma | 2/2 | | ✓ | | | ✓ | | |
| U87 Glioblastoma | 1/1 | | ✓ | | | | | |
| Hep3B Hepatoma | 12/12 | ✗ | ✓ | | | ✗ | ✗ | ✓ |
| PET Mesothelioma | 2/2 | | ✓ | | | ✗ | | |
| REN Mesothelioma | 2/2 | | ✓ | | | ✗ | | |
| YOU Mesothelioma | 2/2 | | ✓ | | | ✗ | | |
| A2780 Ovarian | 6/6[2] | | ✓ | ✓ | | ✓ | ✓ | |
| OVCAR-3 Ovarian | 4/4 | | ✓ | | | | | ✓ |
| AsPC-1 Pancreatoma | 1/2 | | ✗ | | | ✓ | | |
| CFPAC-1 Pancreatoma | 1/10 | | | ✓ | | ✓ | | |
| LNCAP Prostate | 1/1 | | | | ✓ | | | |
| HOSE (Ovarian) | 2/9[3] | ✗ | ✓[4] ✗[6] | ✓ | ✗ | ✗ | ✓[5] ✗[6] | ✓ ✗[6] |

Figure 23:
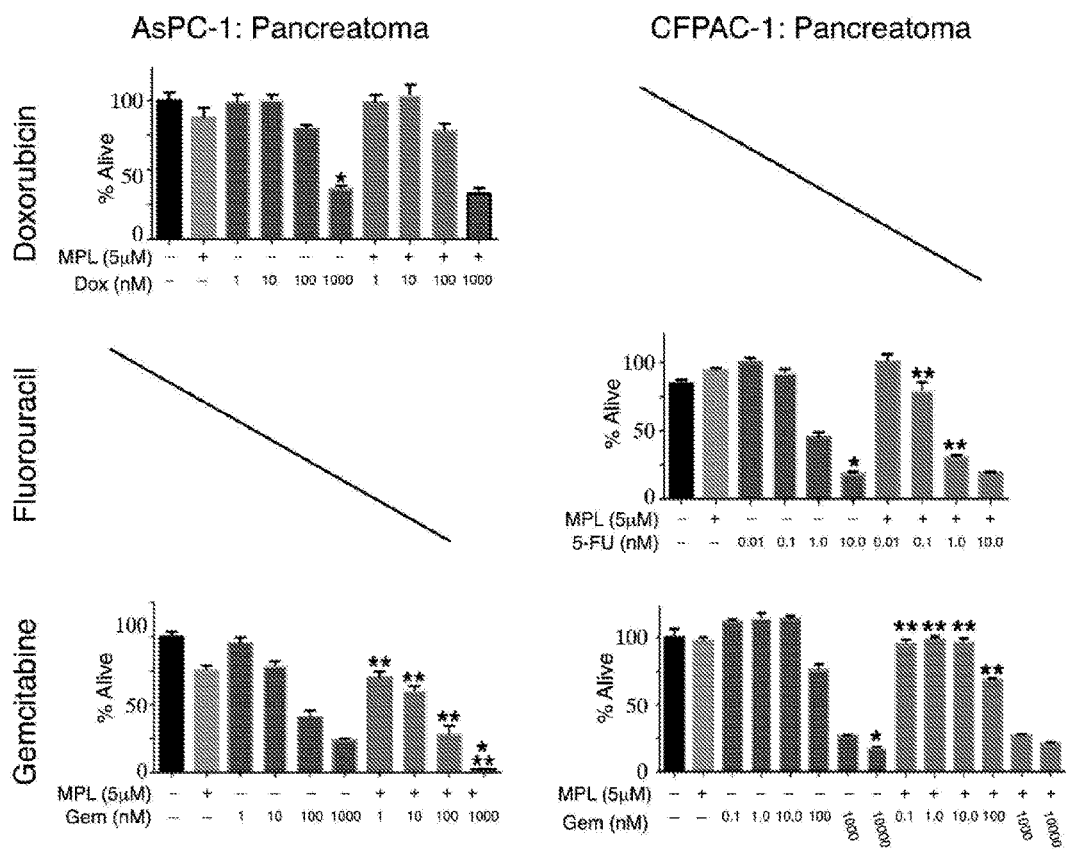
FIG. 23 shows interactions of MPL and doxorubicin, fluorouracil or gemcitabine, upon AsPC-1 and CFPAC-1 malignant cells.
Figure 24:
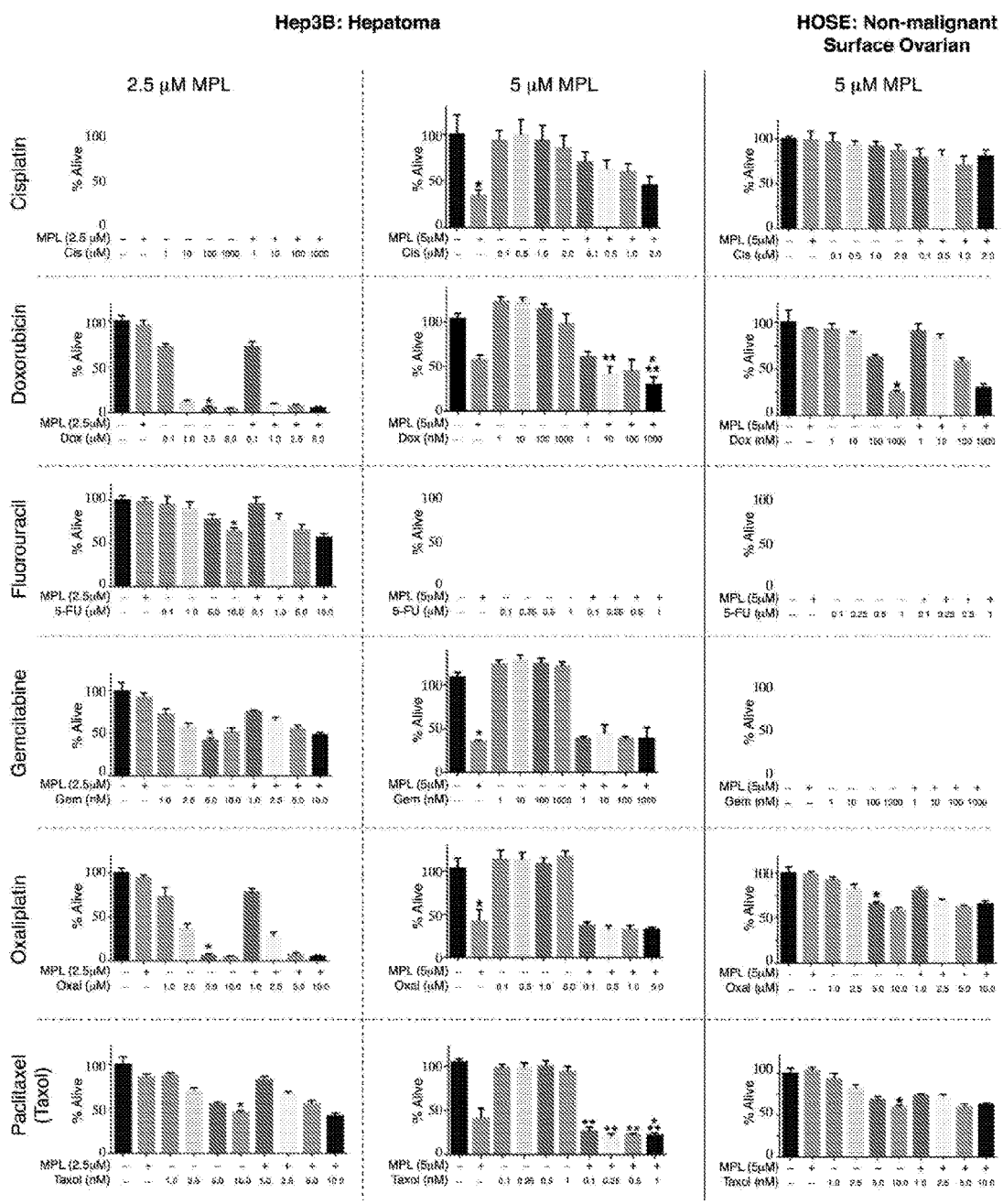
FIG. 24 shows interactions of MPL and cisplatin, doxorubicin, fluorouracil, gemcitabine, oxaliplatin or paclitaxel upon Hep3B malignant cells and HOSE non-malignant cells.

In FIG. 23, MPL and doxorubicin do not display a synergistic interaction upon AsPC-1 cells. MPL and gemcitabine display a strong synergistic interaction upon AsPC-1 cells and do not display a synergistic interaction upon HOSE control cells at these concentrations (see FIG. 22: cytotoxicity against HOSE cells is attributable only to the use of gemcitabine). Similarly, MPL combined with fluorouracil or gemcitabine displays a synergistic interaction upon CFPAC-1 cells. Synergy is not observed for low concentrations of 5-FU upon HOSE cells, but is for high concentrations (see FIG. 22). * indicates the most effective dose, ** indicates synergy.

In FIG. 24, MPL alone at 2.5 µM does not display a cytotoxic effect upon Hep3B cells after 48 h of treatment. MPL alone at 5 µM displays a significant cytotoxic effect upon Hep3B cells after 48 h of treatment in 5 of 5 tests. MPL at 5 µM displays a synergistic cytotoxicity upon Hep3B cells in combination with doxorubicin or paclitaxel after 48 h of treatment. MPL at 5 µM does not display a synergistic cytotoxicity upon HOSE cells in combination with cisplatin, doxorubicin, oxaliplatin or paclitaxel after 48 h of treatment. * indicates the most effective dose, ** indicates synergy.

Figure 25:
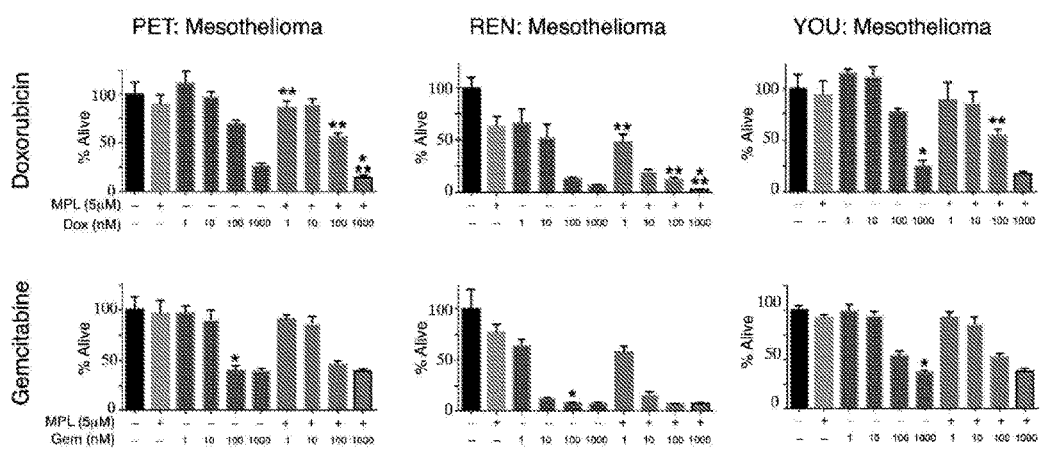
FIG. 25 shows interactions of MPL and doxorubicin or gemcitabine upon PET, REN and YOU malignant cells.

In FIG. 25, MPL and doxorubicin display a synergistic interaction upon PET, REN and YOU mesothelioma cells. MPL and gemcitabine do not display a synergistic interaction upon PET, REN and YOU mesothelioma cells. * indicates the most effective dose, ** indicates synergy.

The inventors have shown that after 72 h of treatment, MPL in combination with: (i) flutamide, synergistically inhibits LNCaP prostatic, and (ii) gemcitabine, synergistically inhibits LN18 glioblastoma, A2780 ovarian and AsPC-1 pancreatic malignant cell line survival rates, without displaying a synergistic interaction at the same concentrations upon non-malignant HOSE control cells (Table 6; LNCAP-1—FIG. 20; LN18—FIG. 21; A2780 and HOSE—FIG. 22; and AsPC1 and C—FIG. 23). Further, and after 48 h of treatment and in combination with either doxorubicin or paditaxel, MPL synergistically inhibits Hep3B cell survival rates, without displaying a synergistic interaction at the same concentrations upon non-malignant and healthy HOSE control cells (Table 6; FIG. 24). In each case, the cytotoxicity observed upon HOSE cells was attributable only to the presence of doxorubicin, flutamide, gemcitabine or paditaxel and not MPL. After 72 h and in combination with relatively low doxorubicin concentrations, MPL displays a synergistic inhibition upon survival rates of: (i) LN18 and U87 glioblastoma; (ii) A2780 and OVCAR-3 ovarian malignant cell lines, and (iii) PET, REN and YOU mesothelioma; but not of non-malignant HOSE cells (Table 6; LN18—FIG. 21; A2780, OVCAR-3 and HOSE—FIG. 22; PET, REN and YOU—FIG. 25). That is, at these low doxorubicin concentrations, cytotoxicity observed upon HOSE cells is attributable only to the presence of doxorubicin. In combination with relatively low oxaliplatin concentrations, MPL displays a synergistic inhibition upon survival rates of A2780 malignant cell lines but not non-malignant HOSE cells. In combination with: (i) fluorouracil, and (ii) paclitaxel, MPL displays a synergistic inhibition upon (i) A2780 ovarian, and (ii) OVCAR-3 ovarian malignant cell lines, respectively, as well as non-malignant HOSE cell survival rates. Whether the combined effect of MPL with fluorouracil and paclitaxel may be significant at a preclinical level requires further investigation.

Further dissection of the effects of MPL drug combinations upon Hep3B cells following 48 h of treatment demonstrates a potent effect of 5 µM MPL alone, irrespective of the combinatorial drug combination (12 of 12 experiments). As described above, 5 µM MPL in combination with either doxorubicin or paclitaxel displays a synergistic cytotoxicity upon Hep3B cell survival rates, and in these experiments, MPL alone displays a strong cytotoxic effect. In combination with cisplatin, gemcitabine or oxaliplatin, however, no synergy is observed due to the high cytotoxicity of 5 µM MPL alone. Furthermore, and in each case, 5 µM MPL does not exert any additive cytotoxic effect upon HOSE cells when combined with either: cisplatin, doxorubicin, oxaliplatin or paclitaxel, at the concentrations tested and after 48h of treatment. MPL (2.5 µM) does not exert a cytotoxic effect upon Hep3B cells in the experiments described here (6 of 6 experiments).

In addition to the cytotoxic drugs listed above, a further four (4) separate cytotoxic drugs have been tested with corresponding HOSE Controls (see Table 7, FIG. 26).

TABLE 7

Synergistic cytotoxicity elicited between MPL and selected cytotoxic drugs on malignant cell lines in vitro.

| Cell Line/Name | Mpl alone Mpl (x/X)[1] Inhibition | Combined Drug Bortezomib | Colchicine | Levamisole | Tamoxifen |
|---|---|---|---|---|---|
| A2780 Ovarian | (4/4) | ✓[2] | ✓ | x | |
| OVCAR-3 | (3/3) | | | ✓[3] | ✓ |
| HOSE (Ovarian) | (0/4) | ✓ | x | x | ✓[4] |

In table 7, Cell lines/name used versus the drug combination. Treatment was with 5 µM MPL and the drug combination for 72 h. In the "Combined Drug" columns, a ✓ indicates synergistic inhibition, while an x indicates no synergistic effect). [1]x=number of events, X=number of experiments. [2]Bortezimib displayed a biphasic response, being synergistic with 5 µM MPL at 0.01, 2.5, 5 and 10 nM but not 0.05, 0.1 or 0.5 nM (two separate experiments). [3]This experiment was repeated. [4]In the Tamoxifen experiment, 2.5 µM MPL was used. The most efficient dose was not determined. Synergy on HOSE cells was not tested at 2.5, 5, 10 and 20 nM Bortezimib. (Bort=Bortezimib; Col =colchicine, Lev=levamisole, Tam—tamoxifen).

In FIG. 26, all treatments times are 72 h. MPL alone at 5 µM displays a significant cytotoxic effect upon all malignant cells tested. MPL at 5 µM displays a synergistic cytotoxicity upon A2780 cells in combination with either: Bortezimib or colchicine. MPL at 5 µM does not display a synergistic cytotoxicity upon A2780 cells in combination with levamisole here but does so against OVCAR-3 cells using levamisole (10 µM) and MPL (5 or 10 µM). See FIG. 16 and Tables 4 and 7). Tamoxifen displays a synergistic cytotoxicity with MPL upon OVCAR-3 cells here. In combination with MPL, Bortezimib and tamoxifen exert a synergistic cytotoxicity upon HOSE cells, but not in combination with colchicine or levamisole here. Note that in combination with tamoxifen upon HOSE cells, 2.5 µM and not 5 µM MPL was used. * indicates the most effective dose, ** indicates synergy. Levamisole dose could be increased.

Bortezimib displays an apparent biphasic response upon A2780 cells, being synergistic with 5 µM MPL at 0.01, 2.5, 5 and 10 nM but not 0.05, 0.1 or 0.5 nM (two separate experiments). HOSE cells treated with 5 µM MPL at 0.01, 0.05, 0.1 and 0.5 nM Bortezimib displayed a synergistic cytotoxicity at 0.01 and 0.05, but not 0.1 or 0.5 nM Bortezimib. Higher Bortezimib concentrations were not tested upon HOSE cells. Colchicine in combination with MPL displayed a cytotoxic effect upon A2780 malignant cells but not non-malignant HOSE cells at the concentrations tested. Levamisole combined with MPL did not display a synergistic effect upon A2780 cells here, however, it is predicted that levamisole at higher concentrations and in combination with MPL may exert a synergistic cytotoxic effect upon A2780 cells. MPL and tamoxifen displayed a synergistic effect upon OVCAR-3 cells at all concentrations tested. Similarly, MPL and tamoxifen displayed a synergistic effect upon HOSE cells, but at half the MPL concentration tested for OVCAR-3 cells. A further 18 separate cytotoxic drugs have been tested in double combination with MPL in other more restricted tests that lacked equivalent HOSE Controls at the same concentrations (see Table 8, below). All but one displayed a synergistic interaction with MPL upon the cell lines tested and at the concentrations tested.

exerted a significant cytotoxic effect upon CFPAC-1 cells in 1 of 10 experiments. In double combination with gemcitabine and fluorouracil, MPL synergistically exerted a cytotoxic effect upon CFPAC-1 cells at low concentrations. MPL was further tested therefore at higher concentrations (10 µM) and in double and triple combinations with gemcitabine and fluorouracil at this higher concentration. MPL (10 µM) alone and at 72 h of treatment, exerted a cytotoxic effect upon CFPAC-1 cells in 4 of 9 experiments (data not shown). In combination with gemcitabine or fluorouracil, 10 µM MPL

TABLE 8

Synergistic cytotoxicity elicited between MPL and selected cytotoxic drugs on malignant cell lines in vitro.

| Cell Line/Name | Mpl alone Mpl (x/X)[1] Inhibition | Combined Drug | | | | | | | | |
|---|---|---|---|---|---|---|---|---|---|---|
| | | A8Z | Amiloride | Atropine | Cimetidine | Cisplatin | EGTA | Enalapril | Etoposide | Everilimus |
| A2780 Ovarian | (3/3) | | | | ✓ | ✓ | | | ✓ | ✓ |
| OVCAR-3 | (5/5) | ✓ | ✓ | ✗ | | | | ✓ | | ✓ |
| HT180 Fibrosarcoma | (1/1) | | | | | ✓ | | | | |

| Cell Line/Name | Mpl alone Mpl (x/X)[1] Inhibition | Combined Drug | | | | | | | |
|---|---|---|---|---|---|---|---|---|---|
| | | Imatinib | Ivermectin | Mifepristone | Mifepristone | Mg132 | Rapamycin | Serotonin | Vincristine | Wortmanin |
| A2780 Ovarian | (5/5) | ✓ | ✓ | ✓ | ✓ | ✓ | ✓ | | ✓ | |
| OVCAR-3 | (2/2)[2] | | | | | | | ✓ | ✓ | | ✓ |

In table 8, Cell lines/names used versus the drug combination. Treatment was with 5 or 10 µM MPL and the drug combination for 72 h. In the "Combined Drug" columns, a ✓ indicates synergistic inhibition, while an ✗ indicates no synergistic effect.). [1]x=number of events, X=number of experiments. [2]MPL alone was used as a control for serotonin and wortmannin in the same experiment.

Example 4

Effects of Pharmaceutical Combination of Monepantel (MPL) in Triple Combination with Various First and Second Line Standard-of-care Chemotherapeutic Drugs The inventors have tested MPL in triple combination with various first and second line standard-of-care chemotherapeutic drugs for synergistic interaction upon malignant cell cytotoxicity using the SRB assay.

Materials and Methods

Cell lines were all obtained from the American Type Culture Collection (ATCC) and maintained as outlined in Example 1 above. The cytotoxicity assays were also performed as outlined in Example 1 above. MPL (5 µM) and combination drugs were applied for 72 h unless indicated.

Results

CFPAC-1 Pancreatoma Cells: MPL, Gemcitabine and Fluorouracil

CFPAC-1 cells represent a pancreatic ductal adenocarcinoma cell line isolated from the liver of a cystic fibrosis patient following metastasis. CFPAC-1 cytotoxicity was assessed by SRB assay following treatment with 5 µM MPL alone and in double combination with gemcitabine or fluorouracil (see Tables 3, 6; FIG. 22). MPL (5 µM) alone synergistically exerted a cytotoxic effect upon CFPAC-1 cells at low concentrations, as observed above (data not shown, see FIG. 23). No further synergy upon CFPAC-1 cytotoxicity was observed from MPL, gemcitabine and fluorouracil triple combination.

Hep3B Hepatoma Cells: MPL, Minocycline, Oxaliplatin and Gemcitabine

Hep3B cells are a hepatitis B containing hepatocellular carcinoma cell line. Hep3B cytotoxicity was assessed by SRB assay following treatment with 5 µM MPL alone and in double combination with cisplatin, doxorubicin, gemcitabine, oxaliplatin and paclitaxel or (see Tables 3, 6; FIG. 24). MPL (5 µM) alone exerted a significant cytotoxic effect upon Hep3B cells in 12 of 12 experiments (Table 6) MPL in combination with both doxorubicin and paclitaxel were synergistically cytotoxic to Hep3B cells (FIG. 24). No synergy was observed in combination with cisplatin, gemcitabine or oxaliplatin: the cytotoxic effect of MPL alone was as strong as the cytotoxic effect in combination.

MPL (5 µM) in double combination with minocycline (5 µM) exerted a synergistic cytotoxicity upon Hep3B cells after 48 h of culture in one (1) of two (2) experiments. Triple combination of MPL with either: (i) minocycline (5 µM) and oxaliplatin (1 µM), or (ii) minocycline (5 µM) and gemcitabine (0.01 µM), did not result in further cytotoxicity to that seen with MPL alone or in double drug combination, respectively (data not shown).

C170 and HT29 Colorectal Carcinoma Cells: MPL. Fluorouracil, Oxaliplatin and Gemcitabine
C170

Figure 27:
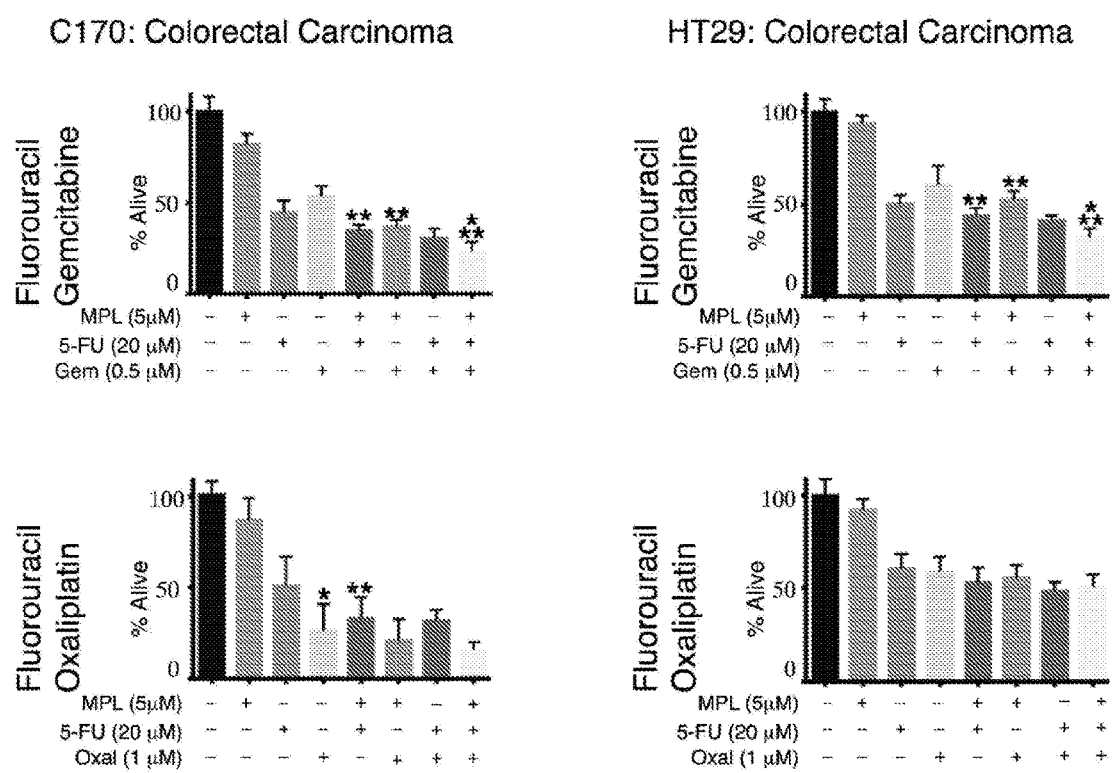
FIG. 27 shows interactions of MPL combined with fluorouracil, gemcitabine or both of fluorouracil and gemcitabine, and MPL combined with fluorouracil, oxaliplatin or both of fluorouracil and oxaliplatin upon C170 and HT29 malignant cells.

The C170 cell line is a colorectal cell line derived from a primary tumour. MPL (5 µM) alone induced a significant cytotoxic effect upon C170 cells in one of two experiments (FIG. 27 and data not shown). In double combination with 5-FU (20 µM; n =2) or gemcitabine (0.5 µM; n=1), MPL (5 µM) exerted a synergistic cytotoxicity upon C170 cells (FIG. 27). No synergistic effect was observed in double combination with oxaliplatin (1 µM; n=1; FIG. 27). In triple combination with 5-FU (20 µM) and gemcitabine (0.5 µM), MPL (5 µM) exerted a further synergistic cytotoxicity upon C170 cells (FIG. 27). No further synergistic cytotoxicity of MPL (5 µM) was observed upon C170 cells in triple combination with 5-FU (20 µM) and oxaliplatin (1 µM).

HT29

The HT29 cell line is a colorectal cell line derived from a primary tumour. MPL (5 µM) alone induced no significant cytotoxic effect upon HT29 cells in two experiments (FIG. 27 and data not shown). In double combination with 5-FU (20 µM; n=1/2) or gemcitabine (0.5 µM; n=1), MPL (5 µM) exerted a synergistic cytotoxicity upon HT29 cells (FIG. 27). No synergistic effect was observed in double combination with oxaliplatin (1 µM; n=1; FIG. 27). In triple combination with 5-FU (20 µM) and gemcitabine (0.5 µM), MPL (5 µM) exerted a further synergistic cytotoxicity upon HT29 cells (FIG. 27). No further synergistic cytotoxicity of MPL (5 µM) was observed upon HT29 cells in triple combination with 5-FU (20 µM) and oxaliplatin (1 µM).

In FIG. 27, the most effective dose for the MPL, 5-FU and oxaliplatin combinations was not determined. * indicates the most effective dose, ** indicates synergy.

OVCAR-3 and SKOV-1 Malignant and HOSE Non-Malignant Ovarian Cells: MPL, Minocycline, Tamoxifen, Paclitaxel and Doxorubicin cell corresponds to the number of experiments performed using that particular drug combination.

OVCAR-3

Figure 28:
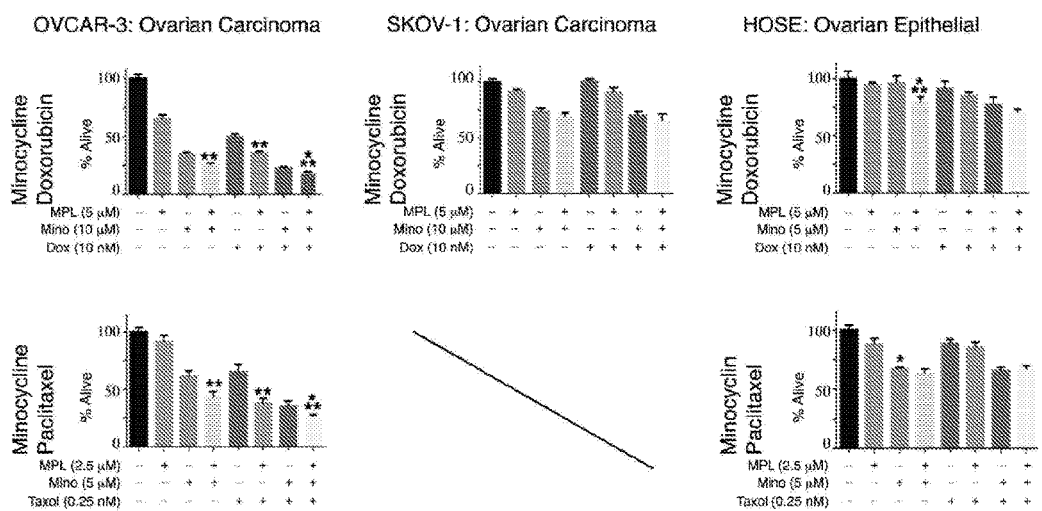
FIG. 28 shows interactions of MPL combined with minocycline, doxorubicin or both of minocycline and doxorubicin, and MPL combined with minocycline, paclitaxel or both of minocycline and paclitaxel upon OVCAR-3 and SKOV-1 malignant cells and HOSE non-malignant cells.

MPL, 5 µM alone (6/6 experiments) but not 2.5 µM alone (1/1 experiments), induces a significant cytotoxic effect upon OVCAR-3 cells (Table 9; FIG. 28). MPL in double combination with minocycline, tamoxifen, taxol (paditaxel) and doxorubicin can exert a synergistic cytotoxic effect upon OVCAR-3 cells (Table 9; FIG. 28). A triple combination of MPL with: (i) minocycline and paclitaxel, or (ii) minocycline and doxorubicin can exert a synergistic toxic effect upon OVCAR-3 cells (Table 9; FIG. 28).

SKOV-1 Cells

MPL, 5 µM alone (3/3 experiments), induced a significant cytotoxic effect upon SKOV-1 cells (Table 9; FIG. 28). MPL in double combination with minocycline (1/3 experiments) and tamoxifen (1/1 experiments) can exert a synergistic cytotoxic effect upon SKOV-1 cells (Table 9; FIG. 28). No synergistic cytotoxicity was observed upon SKOV-3 cells in the MPL triple combination treatments studied here (Table 9; FIG. 28).

HOSE Cells

MPL, 5 µM alone (3/3 experiments) and 2.5 µM alone (1/1 experiments), did not induce a significant cytotoxic effect upon HOSE cells here (Table 9: FIG. 28). MPL in

TABLE 9

Synergistic cytotoxicity elicited between MPL and selected cytotoxic drugs on A2780 and OVCAR-3 malignant and HOSE non-malignant cells in vitro.

A) Single treatment

| Cell Type | MPL (2.5 µM) | MPL (5 µM) | Mino (5 µM) | Mino (10 µM) | Tam (1 µM) | Taxol (5 nM) | Taxol (50 nM) | Taxol (0.25 nM) | Dox (5 nM) | Dox (10 nM) |
|---|---|---|---|---|---|---|---|---|---|---|
| OVCAR-3 | ✗ | ✓✓✓✓✓✓ | ✓✓✓✓ | ✓✓✓ | ✓ | ✓ | ✓ | ✓ | ✓ | ✓ |
| SKOV-1 |  | ✓✓✓ |  | ✓✓✓ | ✓ |  | ✓ |  |  | ✗ |
| HOSE | ✗ | ✗✗✗ | ✓✓✗✗ |  | ✗ |  |  | ✗ | ✗ | ✗ |

B) Double treatment

| Cell Type | MPL Concentration | Mino (5 µM) | Mino (10 µM) | Tam (1 µM) | Taxol (5 nM) | Taxol (50 nM) | Taxol (0.25 nM) | Dox (5 nM) | Dox (10 nM) |
|---|---|---|---|---|---|---|---|---|---|
| OVCAR-3 | 2.5 µM | ✓ |  |  |  |  | ✓ |  |  |
| OVCAR-3 | 5.0 µM | ✓✓✓ | ✓✓✓ | ✓✓ | ✗ | ✗ |  | ✗ | ✓ |
| SKOV-1 | 2.5 µM |  |  |  |  |  |  |  |  |
| SKOV-1 | 5.0 µM |  | ✓✗✗ | ✓ |  | ✗ |  |  | ✗ |
| HOSE | 2.5 µM | ✗ |  |  |  |  | ✗ |  |  |
| HOSE | 5.0 µM | ✓✓✓ | ✗ |  |  |  |  | ✗ | ✓ |

C) Triple Treatment

| Cell Type | MPL Concentration | Mino (5 µM) Tam (1 µM) | Mino (10 µM) Tam (1 µM) | Mino (5 µM) Taxol (5 nM) | Mino (10 µM) Taxol (50 nM) | Mino (5 µM) Taxol (0.25 nM) | Mino (5 µM) Dox (5 nM) | Mino (5 µM) Dox (10 nM) | Mino (10 µM) Dox (10 nM) |
|---|---|---|---|---|---|---|---|---|---|
| OVCAR-3 | 2.5 µM |  |  |  |  | ✓ |  |  |  |
| OVCAR-3 | 5.0 µM | ✗ | ✗ | ✗ | ✗ |  | ✗ |  | ✓ |
| SKOV-1 | 2.5 µM |  |  |  |  |  |  |  |  |
| SKOV-1 | 5.0 µM |  |  | ✗ |  | ✗ |  |  | ✗ |
| HOSE | 2.5 µM |  |  |  |  | ✗ | ✗ | ✗ |  |
| HOSE | 5.0 µM | ✗ |  |  |  |  |  |  |  |

Treatment with MPL and the drug combination was for 72 h. A ✓ indicates synergistic inhibition, while and ✗ indicates no synergistic effect. The number of ✓ 's or ✗ 's per double combination with minocycline and doxorubicin can exert a synergistic cytotoxic effect upon HOSE cells (Table 9; FIG. 28). No synergistic cytotoxicity was observed upon HOSE cells in the MPL triple combination treatments studied here (Table 9; FIG. 28).

In FIG. 28, MPL (5 µM) combined with either (i) minocycline, or (ii) doxorubicin displays a synergistic interaction upon OVCAR-3 cells, but not SKOV-1 cells. MPL (5 µM) combined with minocycline but not doxorubicin displays a synergistic interaction upon HOSE cells. MPL (2.5 µM) combined with either: (i) minocycline, or (ii) paclitaxel displays a synergistic interaction upon OVCAR-3 cells, but not HOSE cells. MPL combined with both minocycline and (i) doxorubicin or (ii) paclitaxel displays a synergistic interaction upon OVCAR-3 cells but not HOSE cells. The most effective dose for the MPL, monocycline and doxorubicin combinations upon SKOV-1 cells was not determined. ** indicates synergy.

Discussion

MPL in vitro and alone displayed a selective and inhibitory effect upon all 28 malignant lines tested (see Example 1). Control HOSE, human fetal astrocytes and HUVEC cells were relatively insensitive to MPL induced cytotoxicity. MPL in vitro and in double combination with known chemotherapeutic drugs displayed a synergistic inhibition upon the survival rates of all malignant cell lines tested (see Example 3). Control HOSE cells were insensitive to MPL in combination with the concentrations of colchicine, flutamide and gemcitabine tested and low concentrations of doxorubicin and oxaliplatin. MPL in vitro and in triple combination with known chemotherapeutic drugs displayed a synergistic inhibition upon the survival rates of C170 and HT29 colorectal (MPL/fluorouracil/gemcitabine) and OVCAR-3 pancreatic (MPL/minocycline/paclitaxel and MPL/minocycline/doxorubicin) malignant cell lines (see Example 4). These data are significant for the individual malignant cell types studied to date for many reasons as set out below.

Breast Cancer MCF-7, MDA-MB-231 and T47-D

Breast cancer is the most frequently diagnosed cancer (approximately 1.7 million in 2012) and the leading cause of cancer death in females worldwide. The most effective treatment is early detection with combined radiotherapy and chemotherapy to reduce tumour size prior to surgery. Despite improvements in the treatment of early stage breast cancer, many women ultimately develop metastatic breast cancer (MBC). MBC is essentially an incurable disease and the prognosis has changed little in the past decade, with the majority of patients succumbing to their disease within two years of diagnosis. Targeted chemotherapeutic drugs for breast cancer include: tamoxifen (an estrogen receptor [ER] antagonist), and trastuzumab, ado-trastuzumab emtansine, perstuzumab and lapitinib (Herceptin; HER-2 epithelial growth factor [EGF] receptor antagonists). Most modern regimens may also encompass anthracyclines and taxanes, often applied in a sequential design. The fact that MBC remains essentially an incurable disease demonstrates that novel classes of therapeutics are required.

MCF-7 and T47-D are ER-positive, progesterone receptor [PR]-positive and HER2-negative anti-estrogen responsive mammary ductal carcinoma lines. MDA-MB-231 is a triple ER/PR/HER-2 negative basal-B mammary carcinoma cell line that is relatively refractory to known chemotherapeutics. All three breast cancer cell lines tested were relatively sensitive to MPL administration with IC50s of 15.5, 23.8 and 5.3 µM, respectively (see Table 3). Triple negative tumours are responsible for 15-25% of all breast cancers and have a considerably high relapse rate. The demonstration that MDA-MB-231 displays a high sensitivity to MPL administration suggests that MPL is a good candidate as an alternative later line therapeutic for such chemo-resistant triple negative representative tumours. The demonstration of particularly high sensitivity of the MCF-7 and T47-D lines similarly suggests that MPL may provide a viable adjunct or later alternative therapy to such estrogen sensitive tumours.

Cervical Cancer: HeLa

Cervical cancer is the third commonest gynecological cancer, with 500 000 new diagnoses each year and accounting for 1.2% of all cancer deaths in women. Five-year survival rates for patients with locally advanced cervical cancer have remained at approximately 70% over the past 20-30 years and new classes of therapeutic are wanting. The addition of platinum-based chemotherapy to radiotherapy has improved outcome compared to radiotherapy alone, however, 30% to 50% of all patients fail to respond to treatment or develop recurrent disease. There are no standard treatment options for these patients, although platinum-based chemotherapy is frequently used and trials are ongoing.

HeLa adenocarcinoma cervical cancer cells were relatively sensitive to MPL administration with an IC50 of 15.8 µM, suggesting that MPL may represent a viable adjunct or alternative therapeutic option.

Colorectal Cancer C170, HCT116, HT29 and HT-29 5 m11

Colorectal Cancer (CRC) is the second commonest reported cancer, with approximately 1.4 million cases worldwide in 2012, and an associated metastatic progression (mCRC) in 50% of all patients with time. Between 1995 and 2006, therapeutic options for mCRC advanced from resection and 5-FU-based therapy to the inclusion of irinotecan, folinic acid, oxaliplatin, bevacizumab, cetuximab and panitumumab treatments. The triple combination of 5-FU, folinic acid and oxaliplatin (FOLFOX) has become an adjuvant standard of care in patients with stage III colon cancer. The inclusion of such options has meant that median overall survival from diagnosis has increased, yet only from an approximate maximum of 9 months to 20 months, with no cure, according to published trials. As a result of these developments, mCRC is now classified as a chronic rather than acute disease, and with the exception of prospective Kras biomarker testing in association with cetuximab treatment, the cost effectiveness and utility of these treatments remains suboptimal or questionable. The case for cost effective treatments that significantly improve patient survival time with minimal side effects is clear.

HT29 and HT-29 5m11 are wild type colon adenocarcinoma cells lines whereas HCT116 is a Kras mutant colorectal carcinoma. Each cell line was relatively highly sensitive to MPL with LC50s of 5.9, 10.4 and 10.5 µM, respectively. With cetuximab and panitumumab displaying little effect upon Kras colorectal tumours and in cases where Folfox, irinotecan and bevacizumab have not provided sufficient effect, MPL may therefore provide a viable further line of therapy.

Glioblastoma: LN18, T98G, U87 and U251

Gliomas are neuroepithelial tumors originating from the supporting glial cells of the central nervous system (CNS) with an incidence of approximately 2 or 3 cases per 100 000 people. Examples of glial tumors include: astrocytomas, oligodendrogliomas, mixed oligo-astrocytic and mixed glioneuronal tumors. Glioblastoma (GBM) multiforme, an astrocytoma, is the commonest and most aggressive malignancy of the brain, accounts for 60-70% of all gliomas, and has two variants: giant cell GBM and gliosarcoma. Without treatment, median survival time following diagnosis of GBM multiforme is 4.5 months. With standard-of-care radiation and temozolomide (TMZ) chemotherapy, median survival is 14.6 months; and with surgery and radiotherapy alone, median survival is 12.1 months. Overall, TMZ combination studies do not currently suggest that one particular chemotherapy combination regimen offers a greater median survival than administration of TMZ alone. Tumor recurrence occurs in 90% of cases at the primary site post-surgery and alternative therapeutic classes are currently lacking.

U87 and U251 GBM cell lines are TPZ sensitive, while LN18 and T98G GBM cell lines are relatively TPZ-insensitive. Regardless of TPZ sensitivity, however, all four GBM lines tested displayed relatively high MPL sensitivity while non-malignant HOSE, human fetal astrocytes and HUVEC control cells were relatively insensitive to MPL. Furthermore, MPL combined with the second round standard-of-care chemotherapeutic drugs doxorubicin and gemcitabine had a synergistic cytotoxic effect upon LN18 and U87 GBM cell lines, while having a higher threshold to effect or no effect, respectively, upon HOSE cells. These data suggest that MPL may offer a viable stand-alone or combination GMB therapeutic when TMZ may have failed.

Hepatoma: Hep3B

Hepatocellular carcinoma (HCC) is the fifth most frequent tumour world-wide, results in between 250,000 and one million deaths globally per annum and has a growing so incidence. Resection or liver transplant are first line treatments for HCC, with radiofrequency ablation also an option, and median overall survival (OS) of 49 months, but high rates of local recurrence. Sorafenib is the only licensed treatment for metastasized or locally uncontrollable HCC and increases median OS from 7.9 to 10.7 months compared to placebo.

Hep3B is a p53 mutant malignant sorafenib sensitive human hepatocellular carcinoma that like HCC is relatively resistant to conventional chemotherapeutic agents such as 5-FU, cisplatin and paclitaxel. Hep3B cells displayed a relatively high sensitivity to MPL treatment alone and synergistic cytotoxic effects were observed when MPL was combined with doxorubicin, minocycline paclitaxel. Ongoing studies are required to determine more precisely the cytotoxicity of MPL combination therapy to healthy tissue, but these data suggest that MPL may offer a viable alternative or supplementary therapeutic to Sorafenib for certain HCC cases.

Mesenchymal Soft Tissue Tumours: Fibrosarcomas and Liposarcomas: HT-1080 and SW-872

Soft tissue sarcomas (STS) are a group of rare and heterogeneous malignant tumours originating from a wide range of mesenchymal cells throughout the body. Surgery represents the only chance of cure, with locally advanced unresectable and metastatic disease is considered generally incurable. Systemic doxorubicin and isosfamide have been the standard first line chemotherapeutics for advanced stage metastatic tumours for more than 30 years and offer an OS of approximately 12-16 months. An urgent need exists for new treatments that improve survival in patients with advanced disease.

Adult fibrosarcoma is a rare and aggressive soft tissue sarcoma, estimated to account for less than 1% of all soft tissue tumours. Surgical resection and radiotherapy provides a 50% to 80% 5-year survival rate, however, chemotherapy for residual or metastatic cells is not established due to the high resistance rate against cytotoxic agents. Liposarcomas are the commonest soft tissue sarcoma with an estimated 2 600 people diagnosed in the US in 2009 and accounting for 20-25% of all sarcomas in adults. Liposarcomas are represented by three main types: well-differentiated/dedifferentiated liposarcomas (WD/DDLPSs), myxoid/round-cell liposarcomas (MLPS), and undifferentiated high-grade pleomorphic liposarcomas (PLPS). PLPS accounts for 5% of liposarcomas and have a high metastatic propensity. Few therapeutic options aside from early detection, surgical removal and radiotherapy of local lesions are available. No current clinical or pathological predictor of outcome exists.

The HT-1080 fibrosarcoma and SW-872 liposarcoma cell lines are doxorubicin, cisplatin and vincristine sensitive cell lines. Both HT-1080 and SW-872 cells were sensitive to MPL treatment, with EC50s of 17.2 µM and 14.7 µM, respectively. These data suggest that MPL may afford a clinically significant effect upon soft tissue sarcomas.

5.7 Mesothelioma: PET, REN and YOU

In the USA, 3 300 cases of malignant pleural mesothelioma and greater than 2 500 related deaths are reported annually. This disease is associated with an approximate 20 to 40 year disease progression latency period following asbestos exposure. The 9/11 terrorist attack deposited 400,000 tons of asbestos on New York and mesothelioma incidences are expected to correspondingly increase. The current best option for cure is extensive excision surgery. Most cases (approximately 80%), however, are presented as late stage and are not candidates for surgical cure. Chemotherapeutic options remain suboptimal with the first-line cisplatin and pemetrexed/raltitrexed combination standard of care therapy offering regression in 15-20% of patients, frequent relapse and median survival of only 12 months; second-line therapy is disappointing.

The relative sensitivity of mesothelioma lines PET, REN and YOU to MPL and the observed synergistic cytotoxic effect of MPL and doxorubicin, suggest that MPL alone or in combination may offer a clinically important effect in a relatively rare but devastating disease.

Ovarian Cancer 1A9, A2780, IGROV-1, OVCAR-3 and SKOV-3

Epithelial ovarian cancer (EOC) is the second commonest gynaecological malignancy and is the leading cause of gynaecological death in women, with 20 000 deaths a year in the USA alone. Surgery and platinum based chemotherapy can be curative at early stages of disease, however, only 40-50% of patients survive five years after diagnosis with advanced EOC, and the majority will succumb to the disease. Approximately 70-75% of patients with EOC are diagnosed at the advanced stage and respond to treatment with surgery and chemotherapy comprising: carboplatin/cisplatin and paclitaxel/docetaxel. The combination of platinum- and taxane-based therapeutics offers an OS increase of 36 months compared to the 24 month OS offered by platinum-based therapies alone. Liposomal doxorubicin, topotecan, gemcitabine, cyclophosphamide and etoposide may also be used dependent upon: platinum insensitivity, patient history, toxicity, cost and/or recurrence. However, the majority of patients develop drug resistance and platinum resistant patients do not respond well to subsequent therapeutics, having a median OS of under 12 months. The use of Bevacizumab in four pivotal phase III trials and anti-angiogenesis and PARP inhibition strategies have shown increased progression free survival (PFS), but less often significant improvements in median OS [e.g. 28.8 v 36.6 months with Bevacizumab]. As such, there is a clear need for new classes of effective EOC therapeutics.

The cisplatin sensitive A2780 and IGROV-1 as well as the cisplatin insensitive 1A29 and OVCAR-3 malignant cell lines all displayed relatively high sensitivity to MPL. The taxol-sensitive and cisplatin- and 5-FU-insensitive p53 mutant SKOV3 cell line displayed a relatively higher resistance to MPL induced cytotoxicity, however it was still considerably more sensitive than the non-malignant control cells. Combination of MPL with: (i) doxorubicin, fluorouracil, gemcitabine and oxaliplatin, and (ii) doxorubicin and paclitaxel, demonstrated a synergistic cytotoxic effect upon A2780 and OVCAR-3 cells, respectively. Additional combinations of MPL with 17 different known cytotoxic drugs demonstrated a synergistic cytotoxic effect upon A2780 and OVCAR-3 cells (see Table 8). These data suggest that MPL may offer a viable alternative or supplementary therapeutic to other less effective classes of therapeutic.

Of interest is that high-grade serous carcinoma (HGSC) is the commonest histological subtype of EOC and druggable pathways include the: (i) GI cell cycle check point, and (ii) PI3K signalling, that are altered in 67% and 45% of cases, respectively. MPL targets the PI3K signalling pathway and as such this class of defect may provide a candidate for a future molecularly targeted approach to therapeutic development.

Pancreatic Cancer: AsPC-1

Early stage pancreatic cancer is generally asymptomatic and therefore diagnosis occurs mostly at locally advanced or metastatic stages. Complete resection is the only potential long-term survival treatment. Since 1997, fluorouracil- and/or gemcitabine-based chemotherapy following resection have represented the standard of care chemotherapeutic agents and have increased median OS by four to seven months. Since their introduction, however, no real advances in OS outcomes have been forthcoming.

AsPC-1 is derived from the ascites of a chemotherapeutic resistant metastatic human pancreatic adenocarcinoma. AsPC-1 cells are highly sensitive to MPL in vitro and display an even greater sensitivity and synergistic cytotoxicity to the standard first in line therapy gemcitabine treatment. HOSE control cells were sensitive to gemcitabine, but MPL did add to the cytotoxicity elicited by gemcitabine. These data suggest that MPL may offer a viable alternative or supplementary therapeutic to gemcitabine for refractory metastatic pancreatic adenocarcinoma, and may do so without causing any additional cytotoxicity, even in the presence of existing gemcitabine therapy.

Prostate Cancer: DU-145, LNCaP, PC-3

Due to the introduction of routine PSA testing for early detection and improved surgical and radiotherapeutic treatment of localised disease, the mortality rate for prostate cancer has been significantly decreasing since 1994. However, 30% of early diagnoses will be recurrent despite surgery and radiotherapy and there remains an inability to treat approximately 80% of cases with metastatic disease. As such, prostate cancer remains responsible for 10% of all cancer deaths in men and is predicted to remain responsible for 30 000 deaths in the US in 2014.

Androgen deprivation therapy is usually provided for surgical and radiotherapeutic refractive disease and is effective for 2-3 years, after which chemotherapy with abiraterone and supuleucel-T may be used to provide approximate four month survival advantages. DU145 PC3 and are metastatic androgen independent malignant prostate cell lines, while the LNCaP cell line is metastatic androgen responsive malignant prostate cell line.

Both PC3 and DU145 cells are sensitive to MPL alone while LNCaP cells are relatively highly sensitive to MPL alone. In combination with the anti-androgen flutamide, MPL exerts a strong synergistic cytotoxic effect while notably having no additive effect upon the cytotoxicity of HOSE cells caused by flutamide. MPL, therefore, may represent a viable alternative or supplementary therapeutic for treatment of androgen-sensitive and even-insensitive disease.

The invention claimed is:

1. A pharmaceutical composition comprising a synergistic combination of at least one aminoacetonitrile derivative, or a metabolite, pharmaceutically acceptable salt, solvate or prodrug thereof, and at least one anticancer compound, or a metabolite, pharmaceutically acceptable salt, solvate or prodrug thereof; wherein the aminoacetonitrile derivative is a pharmaceutical compound of formula (I):

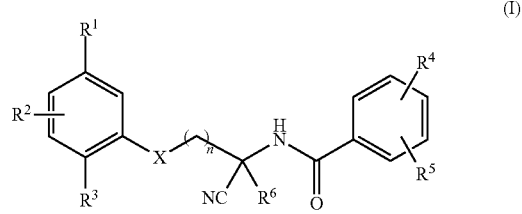

wherein the compound of formula (I) is

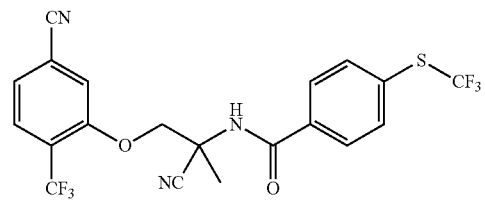 [SMILES: CC(C#N)(COc1cc(C#N)ccc1C(F)(F)F)NC(=O)c1ccc(SC(F)(F)F)cc1]

and wherein the compound of formula (I) is the (R)— or (S)— enantiomer or the racemate; and wherein the anticancer compound is selected from any one or more of doxorubicin, cisplatin, 5-fluorouracil, etoposide, imatinib, mitomycin C, vincristine, paclitaxel, tamoxifen, minocycline, albendazole, levamisole, flutamide, tamoxifen, wortmannin, oxaliplatin, bortezimib, amiloride, EGTA, enalapril, Mg132, captopril, cimetidine, mifepristone, glibenclamide, trifluoperazine, serotonin, clozapine, gemcitabine, ivermectin, colchicine, rapamycin and everolimus.

2. The pharmaceutical composition of claim 1, wherein the compound of formula (I) is N-[(1R)-1-cyano-2-(5-cyano-2-trifluoromethyl-phenoxy)-1-methyl-ethyl]-4-trifluoromethylsulfanyl-benzamide:

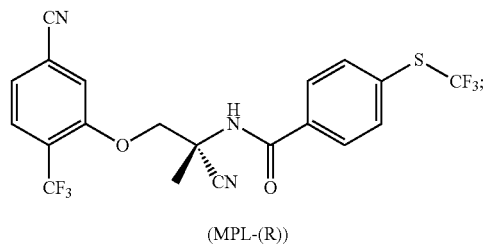

or a metabolite, pharmaceutically acceptable salt, solvate or prodrug thereof.

3. The pharmaceutical composition of claim 1, wherein the compound of formula (I) is MPL (N-[1S)-1-cyano-2-(5-cyano-2-trifluoromethyl-phenoxy)-1-methyl-ethyl]-4-trifluoromethylsulfanyl-benzamide):

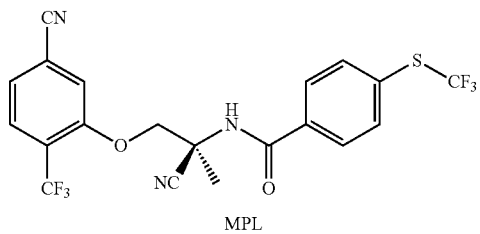 [SMILES: C[C@](C#N)(COc1cc(C#N)ccc1C(F)(F)F)NC(=O)c1ccc(SC(F)(F)F)cc1]

MPL or a metabolite, pharmaceutically acceptable salt, solvate or prodrug thereof.

4. The pharmaceutical composition of claim 1, wherein the anticancer compound is selected from any one or more of doxorubicin, cisplatin, 5-fluorouracil, etoposide, imatinib, mitomycin, vincristine, paclitaxel, tamoxifen, albendazole, levamisole, flutamide, gemcitabine, oxaliplatin, tamoxifen, colchicine and minocycline.

5. The pharmaceutical composition of claim 1, wherein the anticancer compound is doxorubicin.

6. The pharmaceutical composition of claim 1, wherein the composition comprises 5-fluorouracil and gemcitabine.

7. The pharmaceutical composition of claim 1, wherein the composition comprises minocycline and doxorubicin.

8. The pharmaceutical composition of claim 1, wherein the composition comprises minocycline and paclitaxel.

9. A method for the treatment of cancer, the method comprising administering a therapeutically effective amount of the pharmaceutical composition of claim 1.

10. The method of claim 9, wherein the cancer is selected from the following: carcinoma, including that of the bladder, breast, colon, mesothelioma, kidney, liver, lung, including small cell lung cancer, non-small cell lung cancer, head and neck, oesophagus, gall bladder, ovary, pancreas, stomach, cervix, thyroid, prostate, and skin, including squamous cell carcinoma; hematopoietic tumors of lymphoid lineage, including leukaemia, acute lymphocytic leukaemia, acute lymphoblastic leukaemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocyte leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

11. The method of claim 9, wherein the cancer is selected from cancer of the ovaries, breast, prostate or mesothelioma cancer.

12. A method for enhancing the therapeutic efficacy, or reducing the dose or side effects of an anticancer compound in an anticancer regimen, comprising administering a therapeutically effective amount of at least one aminoacetonitrile derivative, or a metabolite, pharmaceutically acceptable salt, solvate or prodrug thereof; wherein the aminoacetonitrile derivative is a pharmaceutical compound of formula (I):

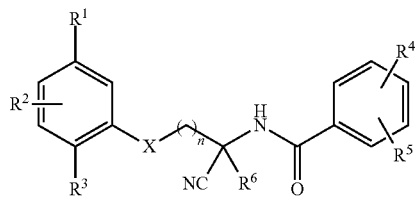

wherein the compound of formula (I) is

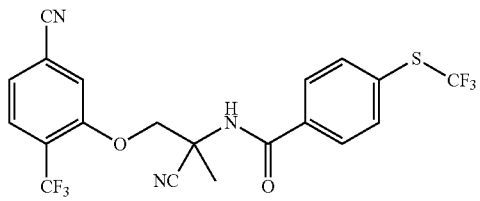 [SMILES: CC(C#N)(COc1cc(C#N)ccc1C(F)(F)F)NC(=O)c1ccc(SC(F)(F)F)cc1]

and wherein the compound of formula (I) is the (R)— or (S)— enantiomer or the racemate; and wherein the anticancer compound is selected from any one or more of doxorubicin, cisplatin, 5-fluorouracil, etoposide, imatinib, mitomycin C, vincristine, paclitaxel, tamoxifen, minocycline, albendazole, levamisole, flutamide, tamoxifen, wortmannin, oxaliplatin, bortezimib, amiloride, EGTA, enalapril, Mg132, captopril, cimetidine, mifepristone, glibenclamide, trifluoperazine, serotonin, clozapine, gemcitabine, ivermectin, colchicine, rapamycin and everolimus.

13. The method of claim 12, wherein the compound of formula (I) is N-[1R)-1-cyano-2-(5-cyano-2-trifluoromethyl-phenoxy)-1-methyl-ethyl]-4-trifluoromethylsulfanyl-benzamide:

AAD 2224

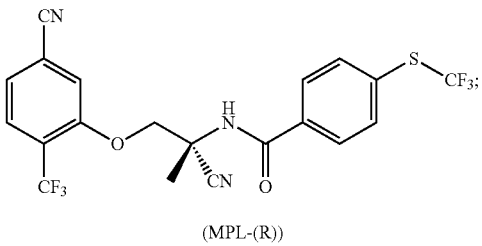

(MPL-(R))

or a metabolite, pharmaceutically acceptable salt, solvate or prodrug thereof.

14. The method of claim 12, wherein the compound of formula (I) is MPL (N-[(1S)-1-cyano-2-(5-cyano-2-trifluoromethyl-phenoxy)-1-methyl-ethyl]-4-trifluoromethylsulfanyl benzamide):

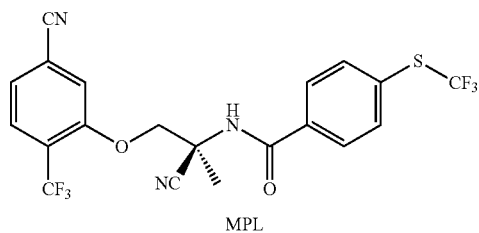 [SMILES: C[C@](C#N)(COc1cc(C#N)ccc1C(F)(F)F)NC(=O)c1ccc(SC(F)(F)F)cc1]
or a metabolite, pharmaceutically acceptable salt, solvate or prodrug thereof.
* * * * *

UNITED STATES PATENT AND TRADEMARK OFFICE
CERTIFICATE OF CORRECTION

PATENT NO. : 9,833,431 B2
APPLICATION NO. : 15/021217
DATED : December 5, 2017
INVENTOR(S) : David Lawson Morris, Mohammad Hossein Pourgholami and Roger Aston It is certified that error appears in the above-identified patent and that said Letters Patent is hereby corrected as shown below:

In the Claims

In Column 43, Claim 3, Line 2 remove "MPL (N-[1S)", and insert -- MPL (N-[(1S) --

In Column 44, Claim 13, Line 44 remove "N-[1R)", and insert -- N-[(1R) --

Signed and Sealed this
Thirtieth Day of January, 2018

Joseph Matal
*Performing the Functions and Duties of the
Under Secretary of Commerce for Intellectual Property and
Director of the United States Patent and Trademark Office*